US006019752A

United States Patent [19]

Sunago et al.

[11] Patent Number: 6,019,752

[45] Date of Patent: Feb. 1, 2000

[54] FLUID VESSEL

[75] Inventors: Seizo Sunago, Osaka; Akira Kagayama, Nara; Osamu Takahata, Osaka; Hitoshi Futagawa, Kusatsu; Mitsuo Murakami, Hyogo; Tomohiko Kubo, Kyoto, all of Japan

[73] Assignees: Fujisawa Pharmaceutical Co., Ltd.; Nissho Corporation, both of Osaka, Japan

[21] Appl. No.: 08/894,087

[22] PCT Filed: Feb. 9, 1996

[86] PCT No.: PCT/JP96/00308

§ 371 Date: Aug. 13, 1997

§ 102(e) Date: Aug. 13, 1997

[87] PCT Pub. No.: WO96/25136

PCT Pub. Date: Aug. 22, 1996

[30] Foreign Application Priority Data

| | | | |
|---|---|---|---|
| Feb. 13, 1995 | [JP] | Japan | 7-24436 |
| Mar. 27, 1995 | [JP] | Japan | 7-68077 |
| Apr. 4, 1995 | [JP] | Japan | 7-79072 |
| Sep. 29, 1995 | [JP] | Japan | 7-253249 |

[51] Int. Cl.[7] .................... A61B 19/00

[52] U.S. Cl. .................... 604/416; 604/403; 220/260; 220/265

[58] Field of Search .................... 206/222; 604/164, 604/403, 82, 416; 220/253, 265, 276, 266, 288, 290, 359.1

[56] References Cited

U.S. PATENT DOCUMENTS

| | | | |
|---|---|---|---|
| 4,623,334 | 11/1986 | Riddell . | |
| 4,735,608 | 4/1988 | Sardam . | |
| 4,756,410 | 7/1988 | Hildebrandt et al. | 206/222 |
| 4,883,468 | 11/1989 | Koussi et al. | 604/164 |
| 4,936,841 | 6/1990 | Aoki et al. . | |
| 5,195,645 | 3/1993 | Schuermann | 220/253 |
| 5,261,902 | 11/1993 | Okada et al. . | |
| 5,308,347 | 5/1994 | Sunago et al. . | |
| 5,352,191 | 10/1994 | Sunago et al. . | |
| 5,662,642 | 9/1997 | Isono et al. | 604/403 |

FOREIGN PATENT DOCUMENTS

| | | |
|---|---|---|
| 61-501129 | 6/1986 | Japan . |
| 63-135642 | 9/1988 | Japan . |
| 2-001277 | 1/1990 | Japan . |
| 4-253863 | 9/1992 | Japan . |
| 4-329956 | 11/1992 | Japan . |
| 4-364850 | 12/1992 | Japan . |
| 6-014976 | 1/1994 | Japan . |
| 6-154289 | 6/1994 | Japan . |
| 6-225920 | 8/1994 | Japan . |
| WO 93/11049 | 6/1993 | WIPO . |

*Primary Examiner*—Corrine McDermott
*Assistant Examiner*—William Noggle
*Attorney, Agent, or Firm*—Oblon, Spivak, McClelland, Maier & Neustadt, P.C.

[57] ABSTRACT

A fluid vessel which include a drug storing chamber, a capping member for hermetically sealing the mouth portion of the drug storing chamber, and a solvent chamber joined to the bottom of the drug storing chamber, wherein the drug storing chamber is provided with a communication hole at the bottom thereof for communicating with the solvent chamber and includes a protruding piece which hermetically seals the communication hole, protrudes into the drug storing chamber, and is movable so as to open the communication hole, while the capping member has an engaging portion to be engaged with the tip of the protruding piece whereby the protruding piece is moved to open the communication hole by rotation of the capping member. This vessel serves to simplify the manufacturing process and reduces the number of components, is readily disposed of, facilitates mixing the drug with the solvent, and is easy to store and handle in hospitals and other facilities.

22 Claims, 13 Drawing Sheets

FLUID VESSEL

TECHNICAL FIELD

The present invention relates to a fluid vessel and, more particularly, to a fluid vessel for preserving a dried drug such as a formulation in the form of powders or a freeze-dried formulation and its solvent in a separate state, and for mixing the dried drug and the solvent in the vessel in a sterile manner just before the use to supply the mixture as a solution for infusion.

BACKGROUND ART

Hitherto, a dried drug contained in a drug vessel such as a vial has been dissolved into a solvent such as distilled water, physiological saline solution, or glucose solution for drip infusion at a medical organization such as a hospital.

For simple and convenient use in such a case, there has been proposed a fluid vessel in which a vial containing a dried drug is connected in series to a solvent vessel containing a solvent, whereby the two vessels are brought into communication in a sterile manner at the time of using.

For example, a fluid vessel 410 disclosed in Japanese Laid-open Patent Publication No. Hei 2(1990 )-1277 is constructed in such a manner that, as shown in FIG. 35, a hollow puncture needle 417 having a hub in the middle and having knife-edges at both ends is interposed between a drug vessel 412 and a solvent vessel 411 containing a solvent, and the puncture needle 417 first pierces the drug vessel 412 and then pierces the solvent vessel 411, whereby the communication between the drug vessel 412 and the solvent vessel 411 can be secured and facilitated and the mixing of the drug and the solvent after the start of communication can be carried out in a short time and in a sterile manner.

The drug vessel 412 is usually sealed with a rubber plug capable of being pierced with the puncture needle 417 and having a self-sealing property. The drug vessel 412 is usually a vial made of glass which is a generally distributed form for dried drugs. The rubber plug is tightly surrounded by a covering member 413 made of aluminum or the like and is fixed onto the mouth portion of the vessel.

Also, there has been proposed a flexible duplex vessel as shown in FIG. 36, in which a plurality of chambers for storing a liquid agent, a powder agent or a solid agent are partitioned with partition means capable of communication (See Japanese Laid-open Patent Publication No. Hei 4 (1992)-364850). This vessel 510 is composed of a plurality of chambers made of flexible sheet, which include a drug solution storing chamber 501, a storing chamber 506 covered with an outer wall 502 and storing a deoxidant 504 and a desiccant 505, and a drug storing chamber 503 covered with an inner wall 508 and storing a drug. These chambers are connected via a weak sealing section 507. The vessel is constructed in such a manner that, at the time of use, the weak sealing section 507 can be easily separated by applying an outer pressure to the drug solution storing chamber 501. This facilitates the communication between the drug solution storing chamber 501 and the drug storing chamber 503. This also facilitates the disposing process of the vessels.

The former fluid vessel 410 has a high applicability and excellent operability because the vessel-uses and incorporates a vial. However, since the vial is made of glass and aluminum, it is difficult to remove and classify the components in disposing the fluid vessels separately after use. Moreover, the components such as the puncture needle 417 and other communication means between the drug vessel

412 and the solvent vessel 411 are complicated and the total number of components is large.

The latter fluid vessel 510 has a drawback that the manufacturing process is complicated since the vessel is formed by sealing a plurality of films. Moreover, since the entire vessel is formed of flexible sheets, the vessel cannot stand by itself and takes a lot of space for storage.

The above-mentioned vessels are usually used for drip infusion, as shown in FIG. 34, by allowing a liquid delivery portion 560 at the bottom of the fluid vessel 550 to be connected to a separate drip infusion device 570 including an insertable puncture needle 561, a tube 562 connected to the puncture needle 561, and a needle portion 563 attached to a tip of the tube 562, a drip infusion barrel 564, and a flow adjusting device 565. Usually, by means of the flow adjusting device 565, the flow can be arbitrarily controlled by pressing the tube 562 housed in the adjusting device case with a roller 566 moving obliquely in the case.

Thus, the adjustment of the fluid can be carried out easily in these fluid vessels. However, in order to supply the adjusted fluid to a patient by drip infusion, it is necessary to separately prepare the above-mentioned drip infusion device 570, to take it out from a sterilized bag, and to insert the puncture needle 561 into the liquid delivery portion 560 at the bottom of the fluid vessel. This involves difficulties and also causes a sterility problem. Moreover, there is a fear that the hands are injured with the puncture needle 561 by mistake in operating the fluid vessel.

The present invention has been made in view of these circumstances and the purpose thereof is to provide a fluid vessel which simplifies the manufacturing process, is readily disposed of, facilitates mixing the drug with the solvent, and allows the drip infusion device to be mounted in a more sterile, safer, and easier manner.

The present invention has been made in view of these circumstances and the main purpose thereof is to provide a fluid vessel and a fluid apparatus which simplify the manufacturing process, are readily disposable, facilitate mixing the drug with the solvent, and are easy to store and handle in hospitals and other facilities, and further allow the drip infusion device to be mounted in a more sterile, safer, and easier manner.

DISCLOSURE OF THE INVENTION

The object of the present invention is to provide a fluid vessel comprising a drug storing chamber, a capping member for hermetically sealing the mouth portion of the drug storing chamber, and a solvent chamber joined to the bottom of the drug storing chamber, characterized in that the drug storing chamber is provided with a communication hole at the bottom thereof for communicating with the solvent chamber and includes a protruding piece which hermetically seals the communication hole, protrudes into the drug storing chamber, and is movable so as to open the communication hole, while the capping member has an engaging portion to be engaged with the tip of the protruding piece whereby the protruding piece is moved to open the communication hole by rotation of the capping member.

Namely, in the present invention, the protruding piece hermetically seals the communication hole provided at the bottom of the drug storing chamber for allowing communication with the solvent chamber and the protruding piece engaged with the capping member is moved by rotation of the capping member to open the communication hole for communication between the drug storing chamber and the solvent chamber.

The drug to be stored in the drug storing chamber of the fluid vessel according to the present invention may be a dried formulation such as a formulation in the form of powders, a granular formulation, a freeze-dried formulation, or the like. Specific examples of the active components in a dried formulation are as follows.

Antibiotics are, for example, cephem antibiotics such as cefazolin sodium, ceftizoxime sodium, cefotiam hydrochloride, cefmenoxime hydrochloride, cephacetrile sodium, cefamandole sodium, cefaloridine, cefotaxime sodium, cefotetan sodium, cefoperazone sodium, cefsulodin sodium, ceftezole sodium, cefpiramide sodium, cefmetazole sodium, cefuroxime sodium, and cefocules sulfate, and penicillin antibiotics such as ampicillin sodium, carbenicillin disodium, sulbenicillin disodium, and ticarcillin sodium and, further, vancomycin hydrochloride. Antitumor agents are, for example, mitomycin C, fluorouracil, tegafur, and cytarabine. Antiulcer agents are, for example, famotidine, ranitidine hydrochloride, and cimetidine.

The solvent to be stored in the solvent chamber of the fluid vessel according to the present invention may be a physiological saline solution, a glucose solution, or an amino acid solution containing cysteine, tryptophan or the like. However, the solvent is not specifically limited thereto.

Specific embodiments of the capping member according to the present invention are those composed of a pierceable plug body and a lid portion optionally attached to the plug body, wherein the end of the plug body includes an engaging portion engaged with the tip of the protruding piece.

According to preferable embodiment of the present invention, a chamber for storing a drug alteration preventive agent may be formed on the capping member hermetically sealing the mouth portion of the drug storing chamber, specifically on the above-mentioned lid portion preferably, so as to store a desiccant and/or a deoxidant inside as the drug alteration preventive agent. The desiccant serves to stabilize the drug which degenerates by humidity and may contain silica gel, zeolite or the like as components. The deoxidant serves to prevent alteration of drugs which are easily oxidized and may contain active iron oxide, amorphous copper or the like. The desiccant and the deoxidant may be suitably used depending on the kind of the drug to be stored in the drug storing chamber. The desiccant and the deoxidant may be used alone or in combination.

The solvent chamber according to the present invention is preferably a flexible vessel formed by fusing a comparatively flexible synthetic resin sheet such as polyethylene, polypropylene or polyvinyl chloride into a bag.

At the bottom of the drug storing chamber according to the present invention, there are provided a communication hole which allows communication of the drug storing chamber with the solvent chamber and a protruding piece which hermetically seals the communication hole and protrudes into the drug storing chamber.

The communication hole may be hermetically sealed by close contact (a contact maintaining the liquid-impermeable property) of the protruding piece, wherein the communication hole may be opened by a sliding movement of the protruding piece accompanying the rotation of the capping member. For example, the communication hole may include two holes formed in axial symmetry or one semicircle-like (semicircular) hole, wherein the protruding piece includes a bottom portion for hermetically sealing these holes in such a manner that the bottom portion can be moved to open the holes. Also, at the bottom of the protruding piece may be formed an opening or a cut portion corresponding to the shape of the communication hole. The opening or the cut portion may be opened to the communication hole by sliding movement accompanying the rotation of the capping member. Further, the protruding piece may be disposed eccentrically from the center of the drug storing chamber and, in correspondence therewith, the engaging portion may be an engagement hole formed at the bottom surface of the plug body, whereby the tip portion of the protruding piece may be inserted into the engaging hole. Specifically, the protruding piece may include a circular bottom plate having an opening closely in contact with and slidingly rotatable on the bottom of the drug storing chamber and a tower-like portion protruding from the bottom plate into the drug storing chamber eccentrically from the center and engaging with the engaging hole of the capping member or its plug body as the engaging portion, whereby the communication hole may be opened by movement of the protruding piece accompanying the rotation of the capping member or its lid portion to allow the opening or the cut portion of the bottom plate to overlap the communication hole.

Further, the communication hole may be hermetically sealed by integrally bonding the protruding piece, whereby the communication hole may be opened by forcible removal of the protruding piece in accordance with the rotation of the capping member.

For example, the communication hole may be constructed as follows. In the state before the use of the fluid vessel, the communication hole is not opened (or formed) because the (foot of the) protruding piece is fitted and integrally bonded. However, the communication hole may be opened (or formed) when the protruding piece (together with the foot) is twisted to be torn off from the bottom by an operation mentioned later.

The protruding piece is preferably molded with resin (preferably molded integrally or welded) at the bottom of the drug storing chamber so that the protruding piece may protrude into the drug storing chamber eccentrically from the center of the drug storing chamber. The protruding piece is preferably a solid or hollow molded member. The protruding piece may be formed of a material having a poor compatibility with the material for forming (the bottom of) the drug storing chamber so that the communication hole may be easily formed when the protruding piece is twisted, whereby the bonded portion liable to be fragile may be cut off, although the material of the protruding piece is not particularly limited thereto.

As a preferable example, the drug storing chamber is formed of polypropylene as a major component, and the protruding piece is formed of a mixture of polyethylene and polypropylene, or an ethylene copolymer or graft polymer as a major component, the drug storing chamber and the protruding piece being welded together.

Here, the capping member is provided with a pierceable plug body, for example made of elastic rubber material, for hermetically sealing the mouth portion of the drug storing chamber as mentioned above and having an engaging portion engaging with the protruding piece of the drug storing chamber. An engaging hole is preferably used as the engaging portion of the plug body. The engaging hole is preferably formed as a pair of holes opposing each other relative to the axial center of the drug storing chamber and, in correspondence therewith, a pair of tower-like portions are formed in the protruding piece. Thus, the plug body is rotated in accordance with the rotation of the capping member, whereby the protruding piece is torn off from the bottom of the drug chamber by twisting via the engaging portion to form the communication hole.

Further, the capping member may be provided with the above-mentioned detachably formed chamber for storing a drug alteration preventive agent and may be provided with a narrow tube portion through the plug body (including the optional lid portion of the capping member) for allowing communication between the chamber for storing a drug alteration preventive agent and the drug storing chamber via a hydrophobic filter. Here, the hydrophobic filter is preferably formed of, for example, a sintered body of polyethylene or polypropylene, polytetrafluoroethylene, or a membrane filter.

According to a preferred embodiment of the present invention, the capping member (or a member mounted on the capping member, for example, a chamber for storing a drug alteration preventive agent; hereafter represented by the capping member) is preferably provided with a self-supporting means for holding the vessel in a self-standing state. The self-supporting means may be formed of a flat portion or a support leg disposed at the head of the capping member. The self-supporting means may be formed integrally with the capping member or be formed so as to cover the capping member.

In summary, according to the fluid vessel of the present invention, when the capping member is rotated with the drug storing chamber hermetically sealed, the protruding member engaging with the engaging portion of the plug body is twisted by rotation of the plug body accompanying the capping member. At this time, the protruding member together with its foot is entirely torn off from the bottom of the drug storing chamber by being twisted, whereby a large communication hole is formed (opened) to allow communication between the drug storing chamber and the solvent chamber. This allows the drug and the solvent to be mixed easily in the vessel.

Preferably, a drug solution delivery portion is provided at the top surface of the capping member and a suspension support portion is provided at the solvent chamber.

The drug solution obtained by mixing the drug with the solvent can be thus taken out as an infusion fluid when an end of the puncture needle of the drip infusion device is connected to the fluid vessel (by piercing) via the plug body of the drug solution delivery portion formed at the top surface of the capping member and the fluid vessel is suspended by using the suspension support portion provided at the solvent chamber with the capping member side facing downwards.

In the present invention, the protruding portion may be formed on the periphery of the communication hole at the bottom of the drug storing chamber so that the protruding portion may integrally protrude into the drug storing chamber via a fragile portion capable of being broken by the rotation of the capping member. Here, the capping member preferably has a leg portion extending into the drug storing chamber so that the tip of the protruding piece may be engaged with the leg portion (for example, engagement by insertion). In such a case, if the leg portion is fitted to receive the protruding piece in assembling the vessel, it is possible to realize communication between the drug storing chamber and the solvent chamber simply by rotating the capping member at the time of carrying out the infusion.

The fragile portion at the bottom of the drug storing chamber according to the present invention refers to a portion which comprises a thin film portion or a groove portion (hollow portion) formed at the bottom of the drug storing chamber and can be easily broken with an external force to allow communication between the drug storing chamber and the solvent chamber.

The protruding piece at the bottom of the drug storing chamber according to the present invention refers to a piece molded with a resin (preferably, molded integrally) at the bottom of the drug storing chamber together with the fragile portion. The protruding piece is preferably a solid or hollow molded member.

The leg portion of the capping member rotates together with the body portion when the capping member is rotated.

According to a preferable embodiment of the present invention, the leg portion of the capping member includes a swollen portion formed in a part of its periphery and radially swollen, and the bottom of the drug storing chamber includes an abutting portion capable of abutting the swollen portion to move the protruding piece after the fragile portion at the bottom of the drug storing chamber is broken by the rotation of the capping member.

The swollen portion is preferably formed integrally with the leg portion at least in some parts of the outer periphery of the leg portion so that the swollen portion may not be easily deformed with a force that does not suffice to break the fragile portion. The abutting portion is preferably formed at a position where a "lever force" acts with the fulcrum being the point of abutment to the swollen portion when the capping member is rotated, preferably near the protruding piece. Preferably, the abutting portion is not easily deformed.

Here, the phrase "to be capable of moving the protruding ing piece" means to be capable of moving the protruding piece outward in a direction substantially perpendicular to its axis on the bottom of the drug storing chamber.

Further, the fluid vessel of the present invention is preferably constructed in such a manner that the body portion and the leg portion of the capping member are formed with their centers spaced apart from each other and the leg portion is fitted to receive the upper portion of the protruding piece, whereby the fragile portion may be broken by moving the upper portion of the protruding piece in a direction tangential to the body portion of the capping member when the capping member is rotated.

Here, the phrase "moving the upper portion of the protruding piece in a direction tangential to the body portion of the capping member" means to rotate the upper portion of the protruding piece with the radius of the rotation being the distance eccentrically away from the body portion of the capping member.

Further, the fluid vessel of the present invention is preferably constructed in such a manner that a threaded portion is formed inside the leg portion of the capping member and a threaded portion in screw engagement with the above-mentioned thread is formed on the protruding piece at the bottom of the drug storing chamber, whereby the fragile portion may be broken by moving the protruding piece in an upward direction when the capping member is rotated.

In the case where the leg portion of the capping member includes a swollen portion and the bottom of the drug storing chamber includes an abutting portion, the protruding piece covering the broken part may be moved in a radial direction after the fragile portion is broken, thus facilitating the flow of the solvent between the drug storing chamber and the solvent chamber.

In the case where the body portion and the leg portion of the capping member are formed with their centers being spaced apart from each other and the leg portion is fitted to receive the upper portion of the protruding piece, the upper portion of the protruding piece is first twisted to break the fragile portion and, further, the upper portion of the protruding piece moves while falling in a direction tangential to the body portion of the capping member when the capping member is rotated, so that the broken part may be enlarged, thus facilitating the flow of the solvent between the drug storing chamber and the solvent chamber.

In the situation where threads to be in screw engagement with each other are formed on the inside of the leg portion of the capping member and on the protruding piece, the two threads are brought into screw engagement with each other to pull the protruding piece in an upward direction when the capping member is rotated and, further, the protruding piece is twisted to break the fragile portion when the capping member is further rotated so that the screw engagement of the two threads reaches the limit. Moreover, since the protruding piece covering the broken part moves in an upward direction while maintaining the screw engagement with the leg portion of the capping member, the flow of the solvent between the drug storing chamber and the solvent chamber is facilitated.

According to another aspect of the present invention, there is provided a fluid apparatus comprising: a drug storing chamber; a capping member serving to hermetically seal the mouth portion of the drug storing chamber and including a body portion and a leg portion which are rotatable; a solvent chamber connected to the bottom of the drug storing chamber in a liquid-impermeable manner and equipped with a drug solution delivery port having a pierceable thin film portion or plug body at a lower end thereof; and a drip infusion device having a needle portion at one end thereof and having, at the other end, a puncture needle capable of piercing the plug body or thin film portion of the solvent chamber, wherein

- the bottom of the drug storing chamber has a fragile portion and a protruding piece protruding into the drug storing chamber and contacting the fragile portion in at least some part of the protruding piece, and the leg portion of the capping member is engaged with the protruding piece so that the fragile portion can be broken by the rotation of the capping member,
- the solvent chamber is engaged with a bottomed outer barrel capable of housing the drip infusion device and capable of displaceably attaching and detaching the drip infusion device, and the puncture needle of the drip infusion device pierces the plug body or thin film portion of the solvent chamber by displacing the outer barrel relative to the solvent chamber after the drug and the solvent are mixed by breaking the fragile portion.

The drip infusion device according to the present invention is a device for injecting into a living body a drug solution (infusion fluid) prepared by mixing the drug and the solvent. The drip infusion device is provided with a puncture needle held near the infusion fluid delivery port of the solvent chamber, a tube for guiding the infusion fluid from the puncture needle, an intravenous injection needle connected to one end of the tube, and a flow adjusting section connected between the puncture needle and the intravenous injection needle for adjusting the amount of dripping flow. The tube is usually made of a flexible transparent tube made of a synthetic resin such as polyvinyl chloride.

The outer barrel is a member constituting the fluid apparatus of the present invention together with the drug storing chamber, the solvent chamber, and the drip infusion device. The outer barrel engages with the solvent chamber to allow the drip infusion device to be stored in a sterile state.

The displacement of the outer barrel relative to the solvent vessel according to the present invention means a change of relative position brought about by the manipulation of the operator so that the drip infusion device housed in the outer barrel may come near the infusion fluid delivery port of the solvent chamber and, further, the drip infusion device may communicate with the solvent chamber via the puncture needle. Therefore, the displacement of the above-mentioned outer barrel may be based on a coupling engagement by pushing one into the other or a screw engagement of these two.

According to a preferable embodiment of the present invention, the outer barrel is engaged slidably on the solvent chamber, and the puncture needle of the drip infusion device pierces the plug body or thin film portion of the solvent chamber by pushing the solvent chamber into the outer barrel after the fragile portion is broken to mix the drug with the solvent.

According to a further preferable embodiment of the present invention, the drip infusion device is equipped with a valve for adjusting the amount of liquid flowing through the tube by switching among a plurality of passageways.

In the fluid apparatus according to the present invention, the solvent chamber has an infusion fluid delivery port at its lower end. This drug solution delivery port is a mouth portion through which the drug solution prepared by mixing the drug with the solvent is taken out as an infusion fluid.

According to the drip infusion device of the present invention, the leg portion of the capping member is rotated to twist the protruding piece engaged with the leg portion when the capping member is rotated with the drug storing chamber being in a hermetically sealed state. At this time, the fragile portion formed in contact with the protruding piece at the bottom of the drug storing chamber is broken because the protruding piece is twisted, thereby allowing a communication between the drug storing chamber and the solvent chamber. Then, the drug and the solvent are mixed and prepared as an infusion fluid by shaking the fluid vessel with the solvent chamber placed in an upper position.

Further, by displacing the outer barrel relative to the drug storing chamber, for example by pushing the drug storing chamber into the outer barrel, the plug body or the thin film portion of the solvent chamber is pierced by the puncture needle of the drip infusion device housed in the outer barrel and held near the drug solution delivery port. Since the drip infusion device is connected to the solvent chamber by this operation, the drip infusion is started by removing the outer barrel from the solvent chamber, opening the valve, and inserting the intravenous injection needle into a blood vessel of a patient.

The drip infusion speed is adjusted by the valve. Since the valve adjusts the amount of liquid flowing through the tube by switching among a plurality of passageways, deformation and poor restoration of the tube by pressing the tube are not observed as in conventional fluid apparatus.

Various other objects, features and attendant advantages of the present invention will be more fully appreciated as the same becomes better understood from the following detailed description when considered in connection with the accompanying drawings in which like reference characters designate like or corresponding parts throughout the several views and wherein:

BEST MODES FOR CARRYING OUT THE INVENTION

A number of Examples according to the present invention are now explained in conjunction with the drawings. These are not to restrict the present invention.

EXAMPLE 1

Figure 1:
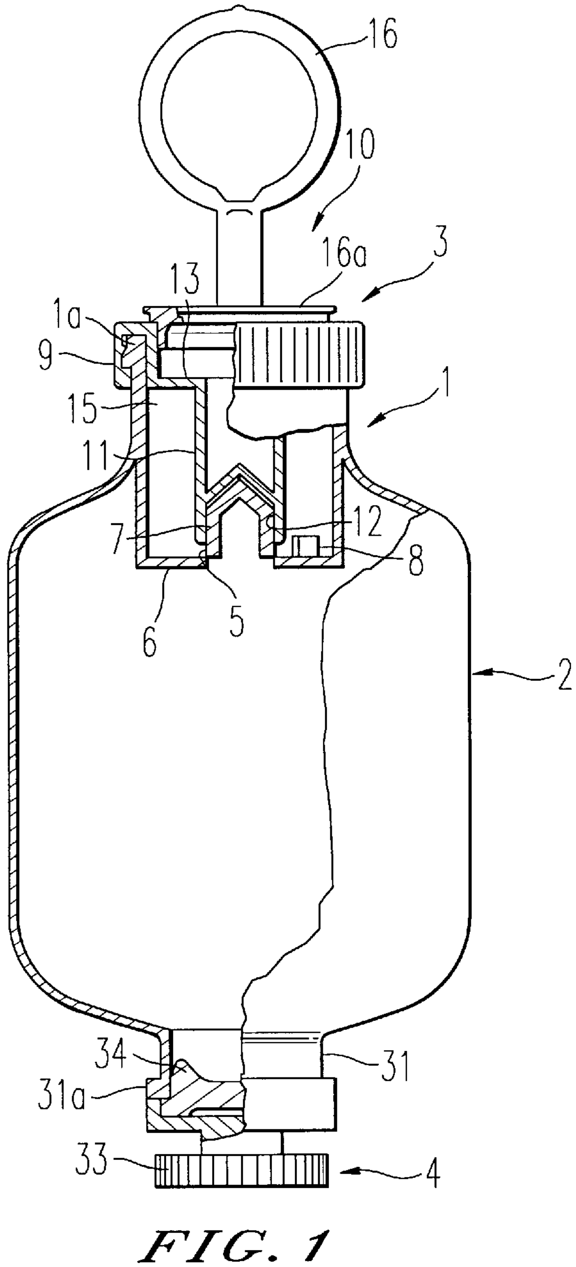
FIG. 1 is a cross-sectional front view of the essential part of the infusion vessel according to Example 1 of the present invention.
Figure 2:
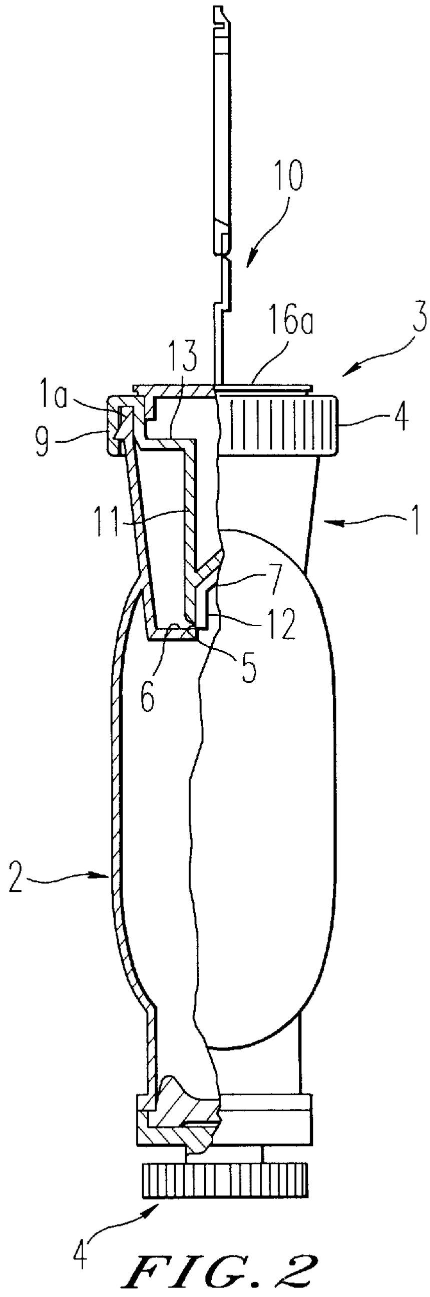
FIG. 2 is a cross-sectional side view of the essential part of the infusion vessel of FIG. 1.

An infusion vessel 10 shown in FIGS. 1 and 2 is mainly constructed with a drug storing chamber 1, a solvent chamber 2, a capping member 3 disposed in the drug storing chamber 1, and a drug solution delivery portion 40.

The drug storing chamber 1 is a vessel having a wide mouth. At an upper end thereof, the drug storing chamber 1 has a mouth portion 1*a* to which the capping member 3 can be mounted and, at a bottom portion 6, the drug storing chamber 1 has a fragile portion 5 mentioned later. The drug storing chamber 1 and the solvent chamber 2 are integrally resin-formed with, for example, polyethylene resin. The solvent chamber 2 is formed to have a comparatively smaller thickness than the drug storing chamber 1 and is capable of being deformed by pressing. A lower end of the drug storing chamber 1 is integrally embedded in an upper portion of the solvent chamber 2.

Figure 3:
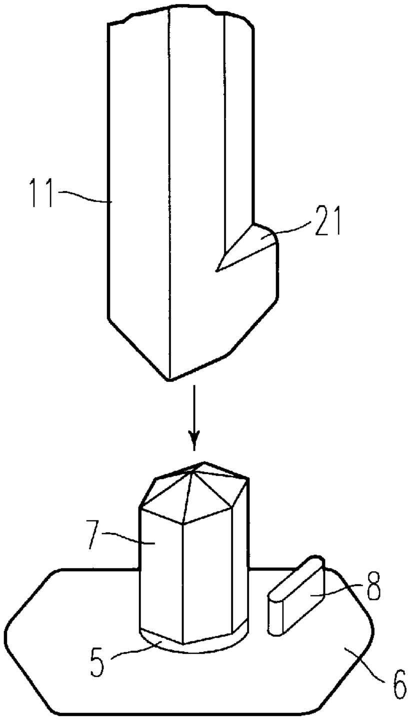
FIG. 3 is a perspective view of the protruding piece and the leg portion in FIG. 1 (in assembling the drug storing chamber).
Figure 4:
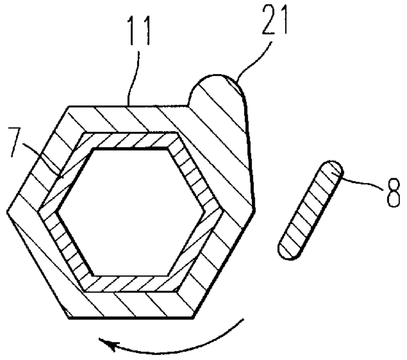
FIG. 4 is a cross-sectional plan view of the protruding piece and the leg portion which are engaged (before the communication is started).

A hollow protruding piece 7 being in contact with the thin film-like fragile portion 5 and protruding into the drug storing chamber 1 side is formed at the drug storing chamber's bottom 6 connecting the drug storing chamber 1 and the solvent chamber 2 in a liquid-impermeable manner. The fragile portion 5 and the protruding piece 7 are integrally formed at the bottom 6 as a part of the drug storing chamber 1 (FIG. 3). The protruding piece 7 is formed in a hexagonal prismatic shape having a pyramid portion at the top. Near the protruding piece 7, a solid abutting portion 8 protruding from the bottom 6 is formed integrally with the bottom 6. The abutting portion 8 is disposed to face obliquely to the axial line of the protruding piece 7 so that the later-mentioned swollen portion 21 abuts thereto and does not slip off between the protruding piece 7 and the abutting portion 8 (FIG. 4). The capping member 3 is constructed with a cap body 9, a leg portion 11 located therebelow and engaged with the protruding piece 7 and a step portion 13. The cap body 9 has a cross section substantially like the letter "T". The upper portion of the cap body 9 is coupled to the outer wall of the drug storing chamber 1 and hermetically seals the mouth portion 1*a* of the drug storing chamber 1 in such a manner that the capping member is itself rotatable. The inside of the cap body 9 is hollow, is kept liquid-impermeable and non-airtight, and stores a desiccant or a deoxidant. Since the inside of the cap body 9 is kept liquid-impermeable, the solvent does not penetrate into the inside of the cap body 9 when the drug storing chamber 1 and the solvent chamber 2 are brought into communication with each other. The leg portion 11 is a hollow member having a hexagonal cross section. A recess 12 having a nesting correspondence with the protruding piece 7 is formed at a lower end of the inside of the leg portion 11. Also, a swollen portion 21 is formed at a lower end of the outer surface of the leg portion 11. As shown in FIG. 4, after the protruding piece 7 engaged with the recess 12 is rotated to break the fragile portion 5 when the leg portion 11 is rotated by the cap body 9 in a direction of an arrow in FIG. 4, the swollen portion 21 abuts with the abutting member 8 to move the protruding piece 7 outward in a direction substantially perpendicular to the axis thereof for driving the protruding piece 7 away from the broken portion.

The drug filling portion 15 for storing the drug is constructed with a cap body 9, an outer surface of the leg portion 11, and an inner surface of the drug storing chamber 1. The moisture or oxygen penetrating into the drug filling portion 15 from outside or from the solvent chamber are adsorbed by the desiccant or deoxidant stored in the inside of the cap body 9 kept non-airtight. After a desiccant or a deoxidant is stored inside the cap body 9, a lid body 16*a* having a suspending device 16 is mounted to its opening edge portion by, for example, thermal welding to provide hermetical sealing.

The drug solution delivery portion 40 is disposed at a lower end of the solvent chamber 2. The drug solution delivery portion 40 is constructed in the same manner as in an ordinary fluid infusion bottle. For example, as shown in FIG. 1, a structure is adopted such that the lower end of the solvent chamber is covered with a fastening member 33 having a knob and a sealing member attached thereto and formed of a rubber plug 34. The sealing member is mounted to the solvent chamber 2 by inserting a rubber plug 34 into the drug solution delivery port 31 and welding a flange 31*a* formed on the outer wall of the delivery portion. The surface of the rubber plug 34 of the sealing member is protected against contamination, and is allowed to appear by twisting and cutting the knob off.

Figure 5:
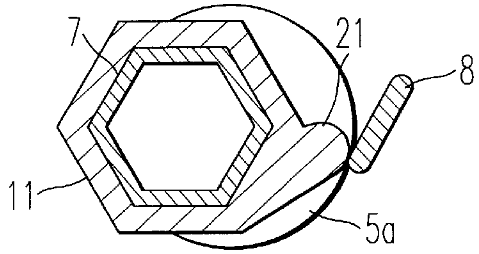
FIG. 5 is a cross-sectional plan view of the protruding piece and the leg portion which are engaged (after the communication is started).

By such a construction, the recess 12 is rotated and the protruding piece 7 is twisted to break the fragile portion 5 when the leg portion 11 is rotated by the cap body 9 (FIG. 4). This allows communication between the drug storing chamber 1 and the solvent chamber 2 and, by pressing the solvent chamber 2, the drug and the solvent are mixed for supplying them as an infusion fluid. Further, the swollen portion 21 abuts against the abutting portion 8, whereby a "lever force" having a fulcrum at the abutting point of the swollen portion 21 and the abutting portion 8 acts on the protruding piece 7 to move the protruding piece 7 covering the broken portion, so that the opening 5*a* of the fragile portion 5 is enlarged (FIG. 5).

The infusion vessel according to this embodiment is constructed in such a manner that the swollen portion 21 and the abutting portion 8 are provided and the protruding piece 7 is moved in a radial direction to enlarge the formed opening 5*a*. However, the above swollen portion 21 and the abutting portion 8 can be omitted and the infusion vessel may have a simple construction such that the leg portion 11 is rotated to twist the protruding piece 7 for breaking the fragile portion 5.

EXAMPLE 2

Figure 6:
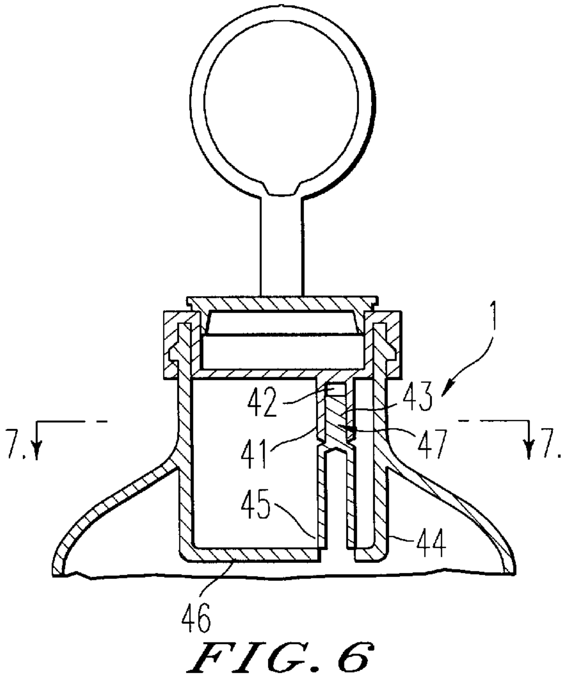
FIG. 6 is a cross-sectional view of an essential part of the protruding piece and the leg portion of the infusion vessel (in assembling the drug storing chamber) according to Example 2 of the present invention.
Figure 7:
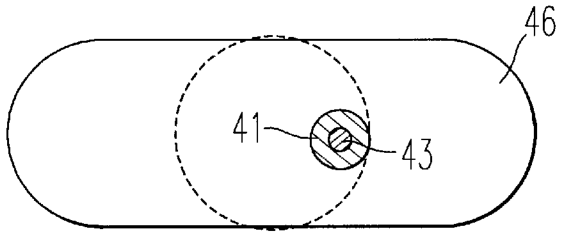
FIG. 7 is a cross-sectional view of FIG. 6 along the line 7—7.
Figure 9:
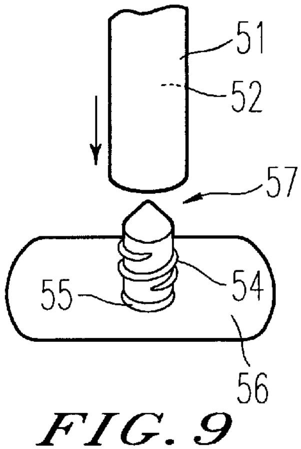
FIG. 9 is a perspective view of the protruding piece and the leg portion of the infusion vessel (in assembling the drug storing chamber) according to Example 3 of the present invention.
Figure 8:
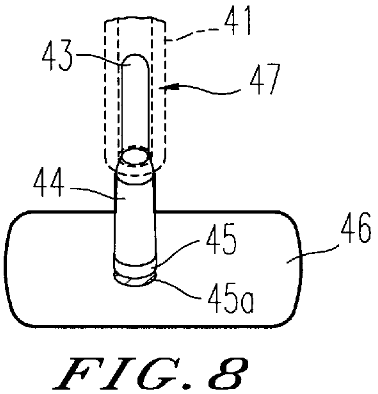
FIG. 8 is a perspective view showing a state in which the fragile portion of FIG. 6 is broken.
Figure 10:
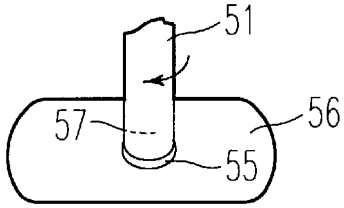
FIG. 10 is a perspective view for explaining the operation of starting the communication by the leg portion of FIG. 9.
Figure 11:
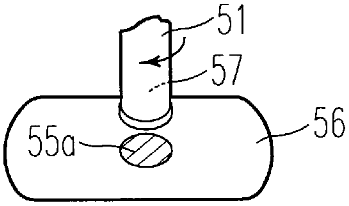
FIG. 11 is a perspective view showing a state in which the fragile portion of FIG. 9 is broken (after the communication is started).

FIGS. 6 to 8 show an example in which a body portion 46 and a leg portion 41 of a capping member 3 are disposed with the centers of their axes spaced apart. The center of the leg portion 41 is formed outside of the center of the body portion 9. The leg portion 41 is a hollow cylindrical member and a recess 42 having a nesting correspondence with a protruding piece 47 is formed inside the leg portion 41.

A thin film-like fragile portion 45 is integrally formed at the bottom 46 of a drug storing chamber 1. A solid protruding piece 47 protruding to the drug storing chamber 1 side is provided at the bottom 46 of the drug storing chamber and in contact with the fragile portion 45. The protruding piece 47 is constructed with a base portion 44 having a large diameter and a tip portion 43 having a small diameter. The leg portion 41 of the capping member 3 is fitted to receive the upper portion of the protruding piece 47, namely, to a position near the foot of the tip portion 43 having a small diameter of the protruding piece 47.

By such construction, the upper portion of the protruding piece 47 first is twisted to break the fragile portion 45 when the leg portion 41 is rotated by the cap body 9. Since the leg portion 41 and the body portion 9 are formed with the centers of their axes spaced apart and the leg portion 41 is fitted to receive the upper portion of the protruding piece 47, the tip portion 43 of the protruding piece 47 moves while falling in a direction tangential to the body portion 9 of the capping member when the body portion 9 is further rotated, whereby the broken portion is enlarged to form a large communication port (opening 45*a*) between the drug storing chamber 1 and the solvent chamber 2 easily.

EXAMPLE 3

Figure 12:
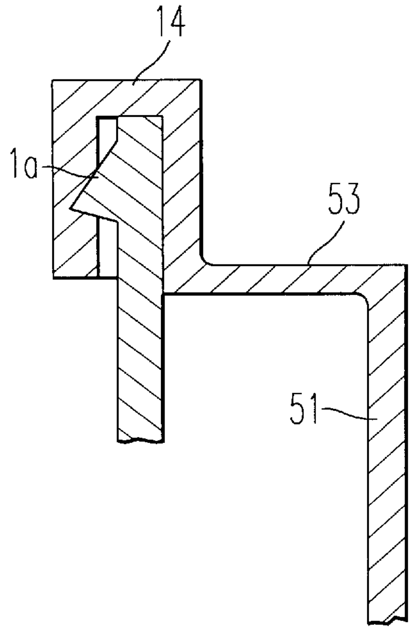
FIG. 12 is a cross-sectional view showing a state of the capping member (before the communication is started).

FIGS. 9 to 13 show an example in which a female screw 52 is formed inside the leg portion 51 of the capping member 3 and the female screw 52 is allowed to be in screw engagement with a male screw 54 formed on the protruding piece 57. The capping members includes a ring portion 14. The leg portion 51 is a hollow cylindrical member and the female screw 52 formed inside thereof has a one-streak thread. At the bottom 56 of the drug storing chamber, there is provided a solid protruding piece 57 protruding to the drug storing chamber 1 side and being in contact with a thin film-like fragile portion 55. The male screw 54 is formed on the perimetric surface of the protruding piece 57. The fragile portion 55 and the bottom 56 are formed integrally as a part of the drug storing chamber 1. In assembling the infusion vessel, the capping member 3 is rotated so that the female screw 52 and the male screw 54 are allowed to be in screw engagement and, as shown in FIG. 12, the capping member 3 is held in a position such that the step portion 53 is substantially horizontal.

Figure 13:
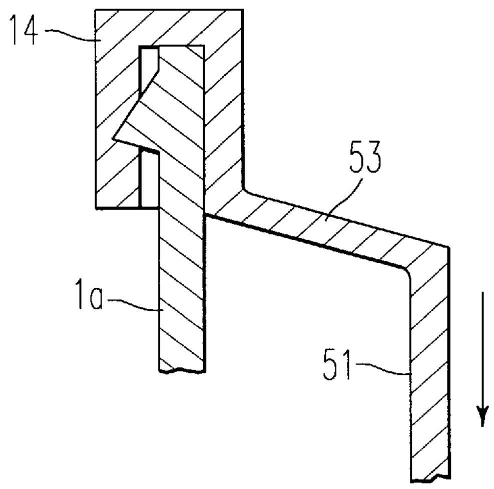
FIG. 13 is a cross-sectional view showing a state of the capping member (in carrying out the operation of starting the communication).

In this construction, when the leg portion 51 is rotated by the cap body 9, the protruding piece 57 is pulled upwards according as the screw engagement between the female screw 52 and the male screw 54 increases. Next, when the lower end of the leg portion 51 approaches near the bottom 56 (FIG. 10), the female screw 52 reaches the foot of the male screw 54 to terminate the screw engagement of the screws 52 and 54. At this time, the step portion 53 comes to a state of being inclined downwards from the state of being substantially horizontal (FIG. 13). When the cap body 9 is further rotated, the protruding piece 57 is twisted.

At this time, since the fragile portion 55 is in a state of being pulled upwards in an axial direction, the fragile portion 55 is cut easily when the protruding piece 57 is twisted (FIG. 12). Further, a gap is generated between the protruding piece 57 and the opening 55*a* since the cut protruding piece 57 is lifted upwards by the repulsion of the step portion 53 while being engaged with the female screw 52 on the inside the leg portion 51. This forms a comparatively large communication port (opening 55*a*) between the drug storing chamber 1 and the solvent chamber 2, whereby the drug is mixed with the solvent smoothly.

Figure 14:
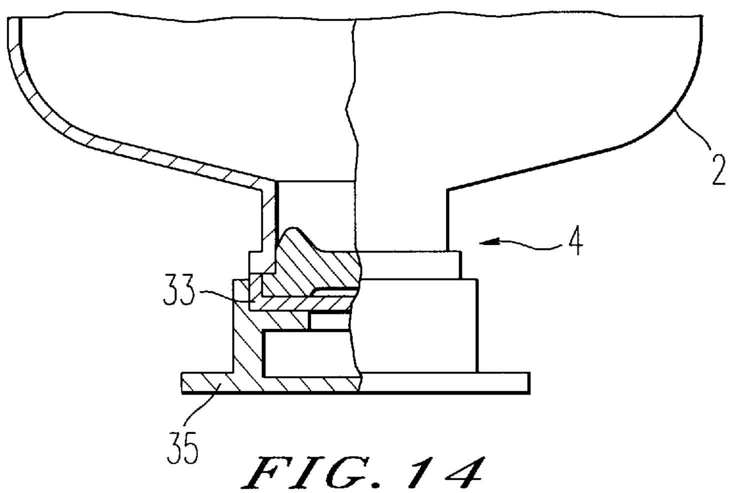
FIG. 14 is a cross-sectional front view of an essential part of an embodiment of the self-supporting means provided in the drug solution delivery portion.

In order to allow the infusion vessels of the above Examples 1 to 3 to stand by themselves, it is preferable to use a stand 35 as shown in FIG. 14. The stand 35 is mounted, for example, to the knob portion of the fastening member 33 be press fitting.

Thus, in the present invention, the communication between the drug storing chamber 1 and the solvent chamber 2 can be achieved with extreme ease by the rotation of the capping member or by pressing the lid member or the solvent vessel.

As shown above, since the fragile portion contacting the protruding piece can be broken by rotating the capping member at the mouth portion of the drug storing chamber in the infusion vessel of the present invention, the drug storing chamber and the solvent chamber can be brought into communication easily to mix the drug and the solvent.

In case the leg portion of the capping member is formed to be capable of being fitted to receive the protruding piece, the fragile portion can be broken at a time with certainty simply by rotating the capping member in starting the infusion.

In the situation where the leg portion of the capping member has a swollen portion and an abutting portion abutting to the swollen portion is provided, the protruding piece covering the broken portion can be moved after the fragile portion is broken, whereby a larger communication port can be formed between the drug storing chamber and the solvent chamber. Therefore, the drug is mixed with the solvent more easily.

In case the body portion and the leg portion of the capping member are formed with their centers spaced apart from each other and the leg portion is fitted to receive the upper portion of the protruding piece, the tip portion of the protruding piece is twisted to break the fragile portion when the capping member is rotated and, after the fragile portion is broken, the tip portion of the protruding piece moves while falling in a direction tangential to the body portion of the capping member. Therefore, the broken portion can be enlarged and a larger communication port can be formed between the drug storing chamber and the solvent chamber, whereby the drug is mixed with the solvent easily.

Where a screw engagement is formed between the leg portion and the protruding piece of the capping member, it is possible to move the protruding piece covering the broken portion in an upward direction after the fragile portion is broken while maintaining the screw engagement with the leg portion of the capping member. Therefore, a larger communication port can be formed between the drug storing chamber and the solvent chamber, whereby the drug is mixed with the solvent easily.

If a desiccant and/or a deoxidant is stored in the inside of the body portion of the capping member, it is possible to maintain the dry state of the drug which is liable to degenerate by moisture, thereby preventing the change with the passage of time of the drug having a tendency of being oxidized easily.

Where the solvent chamber of the infusion vessel is provided with a drug delivery portion at a lower end thereof, the drug solution obtained by mixing the drug with the solvent can be easily taken out as an infusion fluid.

In case the drug storing chamber of the infusion vessel is provided with a self-supporting means for allowing the vessel to stand by itself, it is possible to store the infusion vessels or to allow them to be on standby in arrangement, whereby the infusion vessels can be handled with ease.

Since the infusion vessels of the present invention can be integrally molded, the manufacturing process can be simplified, and besides, a complex structure for connecting the drug storing chamber with the solvent chamber can be omitted and the number of components can be reduced, making it possible to provide infusion vessels at low prices. Also, the transportation costs can be lowered and the storage space can be secured easily.

Furthermore, since neither glass vial nor double-edged needle is used, there is no fear of injuring the hands by mistake. Also, since neither glass nor aluminum is used, it is unnecessary to classify the components in discarding the infusion vessels, thereby facilitating the discarding process.

EXAMPLE 4

Figure 15:
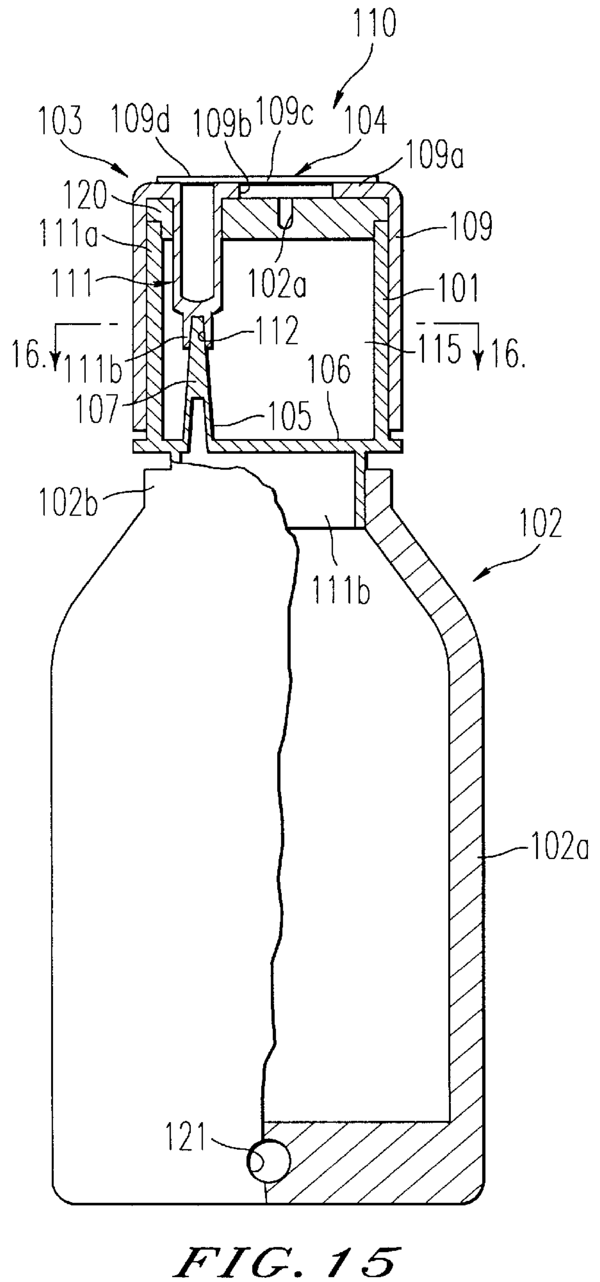
FIG. 15 is a cross-sectional front view of an essential part of the infusion vessel according to Example 4 of the present invention.
Figure 16:
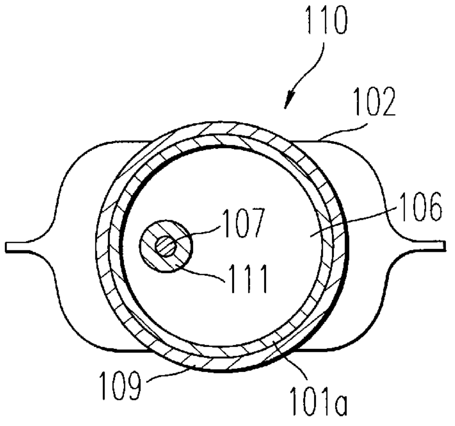
FIG. 16 is a cross-sectional view of FIG. 15 along the line 16—16.

A infusion vessel 110 shown in FIGS. 15 and 16 is mainly constructed with a drug storing chamber 101, a solvent chamber 102, a capping member 103 disposed in the drug storing chamber 101, and a drug solution delivery portion 104.

The drug storing chamber 101 is a wide-mouth vessel including, at the upper end thereof, a mouth portion 101*a* to which the capping member 103 can be mounted and, at the bottom portion 106, a fragile portion 105 mentioned later. The drug storing chamber 101 is integrally resin-molded with, for example, polyethylene resin.

The solvent chamber 102 is formed into a liquid-impermeable bag-like shape by stacking transparent polyethylene resin sheets and fusing the peripheral portions 102*a*, so that the solvent chamber 102 has sufficient flexibility. At an upper portion of the solvent chamber 102, there is formed a mouth portion 102*b* which is connected to a port 101*b* formed at the lower portion of the drug storing chamber 101. At a peripheral portion 102*a* of a lower end of the solvent chamber 102, there is formed a suspending hole 121 as a suspension support portion. The drug storing chamber 101 and the solvent chamber 102 are connected by, for example, heat-welding the port 101*b* of the drug storing chamber 101 and the mouth portion 102*b* of the solvent chamber 102. Alternatively, the drug storing chamber 101 and the solvent chamber 102 may be integrally resin-molded.

Figure 17:
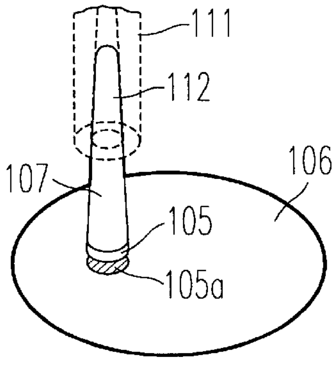
FIG. 17 is a perspective view showing a state in which the fragile portion of FIG. 15 is broken.

At the drug storing chamber's bottom portion 106 connecting the drug storing chamber 101 and the solvent chamber 102 in a liquid-impermeable manner, there is provided a solid conical protruding piece 107 being in contact with the thin film-like fragile portion 105 and protruding into the drug storing chamber 101 with the center of the protruding piece 107 shifted from the center of the vessel. The protruding piece 107 is formed integrally with the bottom portion 106 as a part of the drug storing chamber 101 (FIG. 16 and FIG. 17).

The capping member 103 is constructed with a cap body 109 and a leg portion 111 protruding inwards from the lid portion 109*a* thereof and having a lower end which engages with the protruding piece 107. The lower portion of the inside wall of the cap body 109 is coupled to the outer wall of the drug storing chamber 101 and hermetically seals the mouth portion 101*a* of the drug storing chamber 101 so that the cap body 109 is itself rotatable. In the lid portion 109*a* of the cap body 109, there is formed a cut hole 109*b* capable of being pierced by a puncture needle connected to one end of the drip infusion device. Also, the upper portion of the lid portion 109*a* includes a flat surface which allows the infusion vessel 110 filled with a drug and a solvent to stand by itself.

A rubber plug 120 is inserted between the cap body 109 and the mouth portion 101*a* so as to maintain the drug storing chamber 101 airtight. Approximately at the center of the rubber plug 120, there is formed a recess 120*a* being in corresponding with the cut hole 109*b* and facilitating the piercing of the puncture needle. Though the recess 120*a* is exposed at the cut hole 109*b* portion, the cut hole 109*b* portion of the lid portion 109*a* is protected by a film 109*c* so that the surface of the rubber plug 120 may not be contaminated. The recess 120*a* appears when the film 109*c* is peeled off.

The leg portion 111 is a hollow member constructed to have substantially a cylindrical shape. The leg portion 111 is constructed with a chamber 111*a* for storing a drug alteration preventive agent, the chamber 111*a* extending downwards to be connected with the lid portion 109*a*, and an engaging portion 111*b* extending further downwards from the lower end of the chamber 111*a* for storing a drug alteration preventive agent. The lid portion at the upper end of the chamber 111*a* for storing a drug alteration preventive agent is open and stores a desiccant or a deoxidant inside. The engaging portion 111*b* has a recess 112 formed in nesting correspondence with the protruding piece 107. The tip portion of the protruding piece 107 is inserted into the recess 112 of the leg portion 111.

The chamber 115 for storing a drug is formed with the inside surface of the cap body 109, the rubber plug 120, and the bottom portion 106. Moisture or oxygen penetrating from the outside or from the solvent chamber into the drug filling portion 115 are adsorbed by a desiccant or a deoxidant stored in a desiccant filling portion 111*a* which is inside the leg portion 111 maintained to be non-airtight. The drug storing chamber 101 is hermetically sealed by attaching a cover film 109*d* onto the peripheral portion of the opening by means of heat-welding or the like after loading a drug into the drug filling portion 115, coupling the capping member 103 having the rubber plug 120 therein with the mouth portion 101*a*, and then storing the desiccant or the deoxidant into the chamber 111*a* for storing a drug alteration preventive agent.

By the above-described construction, when the leg portion 111 is rotated by the cap body 109 in using the infusion vessel, the upper portion of the protruding piece 107 is first twisted to break the fragile portion 105. Since the leg portion 111 and the cap body portion 109 are formed with the centers of their axes spaced apart and the leg portion 111 is fitted to receive the upper portion of the protruding piece 107, the upper portion of the protruding ing piece 107 moves while falling in a direction tangential to the body portion 109 of the capping member when the body portion 109 is further rotated. This enlarges the broken portion, whereby a large communication hole (opening 105*a*) is easily formed between the drug storing chamber 101 and the solvent chamber 102.

After the drug is mixed with the solvent by pressing the solvent chamber 102, the film 109*c* is peeled off; the cut hole 109*b* of the drug solution delivery portion 104 is pierced with the puncture needle connected to one end of the drip infusion device to pierce the rubber plug 120; the suspending hole 121 of the solvent chamber 102 is hung onto a stand, whereby the drug solution obtained by mixing the drug with the solvent can be taken out as an infusion fluid from the other end of the drip infusion device. Here, if the vessels 110 are permitted to stand by themselves with the flat surface of the lid portion 109*a* facing downwards, it is possible to store the infusion vessels or to allow them to be on standby in arrangement.

Thus, in the above Example, communication between the drug storing chamber 101 and the solvent chamber 102 can be achieved with extreme ease by the rotation of the capping member 103.

Since the upper surface of the lid portion 109*a* includes a flat surface which allows the vessel 110 filled with a drug and a solvent to stand by itself, the infusion vessels can be stored or allowed to be on standby in arrangement, so that the handling of the vessel 110 is facilitated.

Since the drug solution delivery portion 104 is formed integrally with the capping member 103, it is unnecessary to perform the step of separately preparing and attaching a drug solution delivery portion onto the lower portion of the solvent chamber by fusion or the like as in a conventional method.

Also, it is unnecessary to mold the suspension support portion integrally with the capping member or to furnish them by bonding, so that the vessel 110 can be suspended simply by opening a hole 121 at a lower portion of the solvent chamber 102.

As shown above, according to the infusion vessel of the present invention, the fragile portion contacting the protruding piece can be broken by rotating the capping member at the mouth portion of the drug storing chamber, whereby the drug storing chamber and the solvent chamber can be easily brought into communication with each other to mix the drug with the solvent.

In the case where the leg portion of the capping member is formed to be capable of being fitted to receive the protruding piece, the fragile portion can be broken at a time with certainty simply by rotating the capping member at the time of use.

In the situation where the center of the leg portion of the capping member is formed so as to be shifted from the center of the body portion and the leg portion is fitted to receive the upper portion of the protruding piece, the upper portion of the protruding piece is first twisted to break the fragile portion when the capping member is rotated, and after the fragile portion is broken, the tip portion of the protruding piece moves while falling in a direction tangential to the body portion of the capping member. This enlarges the broken portion and forms a larger communication hole between the drug storing chamber and the solvent chamber, whereby the drug can be mixed with the solvent easily.

According to the present invention, since the drug solution delivery portion is formed integrally with the capping member, it is unnecessary to perform a step of separately preparing and attaching a drug solution delivery portion onto the lower portion of the solvent chamber as in a conventional method. Also, it is unnecessary to mold the suspension support portion integrally with the capping member or to furnish them by bonding, so that the vessel can be suspended simply by, for example, opening a hole for suspending as a suspension support portion at a lower portion of the solvent chamber for application to infusion.

According to the infusion vessels of the present invention, the manufacturing process can be simplified, and besides, a complex structure for connecting the drug storing chamber with the solvent chamber can be omitted and the number of components can be reduced, thus making it possible to provide infusion vessels at low prices. Also, the transportation costs can be lowered and the storage space can be secured easily.

Furthermore, since neither a glass vial nor a double-edged needle is used, there is no fear of injuring the hands by mistake. Also, since neither glass nor aluminum is used, it is unnecessary to classify the components in discarding the infusion vessels, thereby facilitating the discarding process.

EXAMPLE 5

Figure 18:
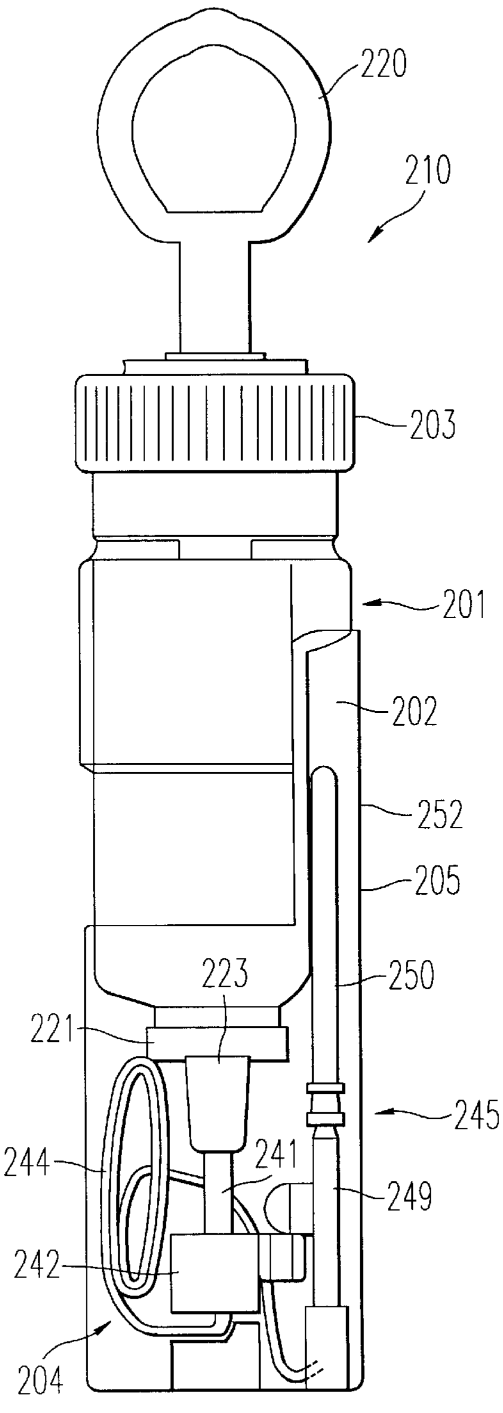
FIG. 18 is a front view of the infusion apparatus according to Example 5 of the present invention.
Figure 19:
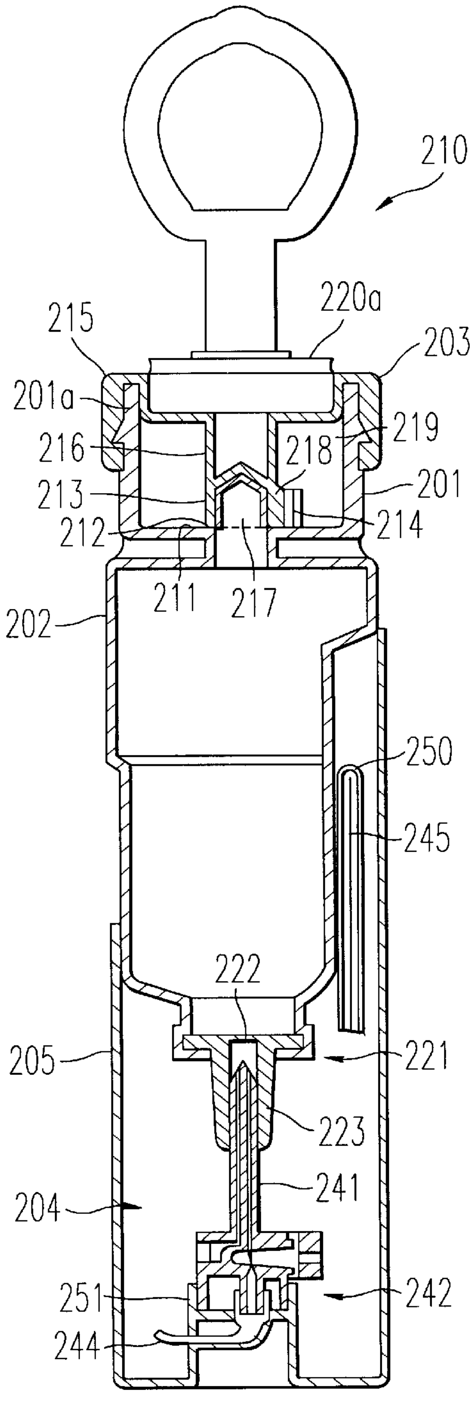
FIG. 19 is a cross-sectional view of an essential part of the infusion apparatus of FIG. 18.

A infusion vessel 210 shown in FIGS. 18 and 19 is mainly constructed with a drug storing chamber 201, a solvent chamber 202, a drip infusion device 204, and an outer barrel 205.

Figure 20:
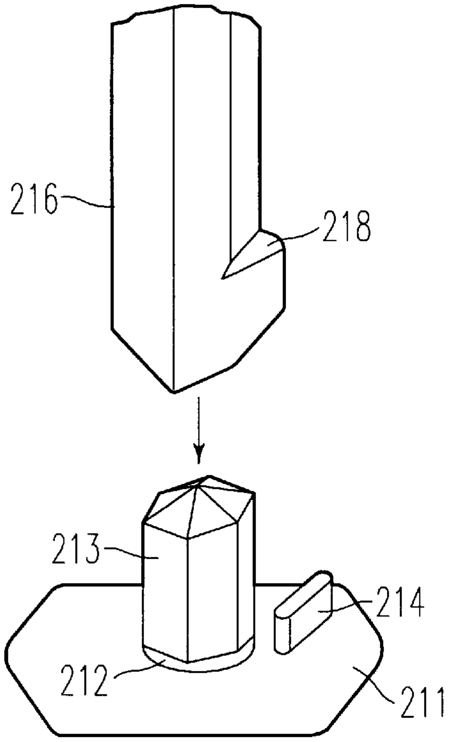
FIG. 20 is a perspective view of the protruding piece and the leg portion in FIG. 18.
Figure 21:
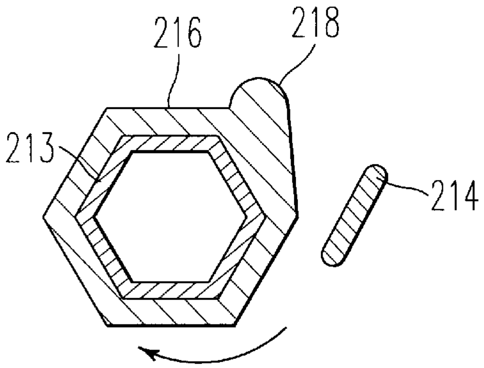
FIG. 21 is a cross-sectional plan view of the protruding piece and the leg portion which are engaged (before the communication is started).

The drug storing chamber 201 is a wide-mouth vessel including, at the upper end thereof, a mouth portion 201*a* to which a capping member 203 can be mounted and, at the bottom portion 211, a fragile portion 212 mentioned later. The drug storing chamber 201 and the solvent chamber 202 are a cylindrical vessel integrally resin-molded with polyethylene resin, and is formed to have a thickness which will not allow the vessel to be deformed easily by a pressing force from outside. At a drug storing chamber's bottom 211 for allowing communication between the drug storing chamber 201 and the solvent chamber 202 in a liquid-impermeable manner, there is provided a hollow protruding piece 213 contacting the thin film-like fragile portion 212 and protruding to the drug storing chamber 201 side. The fragile portion 212 and the protruding piece 213 are formed integrally at the bottom portion 211 as a part of the drug storing chamber 201 (FIG. 20). The protruding piece 213 is formed in a hexagonal prismatic shape having a pyramid portion at the top. Near the protruding piece 213, a solid abutting portion 214 protruding from the bottom portion 211 is molded integrally with the bottom portion 211. The abutting portion 214 is disposed to face obliquely to the axial line of the protruding piece 213 in order that one end of the abutting portion forms a narrow passageway for the protruding piece 213 so that the later-mentioned swollen portion 218 abuts thereto and does not slip off between the protruding piece 213 and the abutting portion 214 (FIG. 21).

The capping member 203 is constructed with a cap body 215 and a leg portion 216 disposed therebelow and engaging with the protruding piece 213. The cap body 215 has a cross section substantially in the shape of the letter "T". The upper portion of the cap body 215 is coupled to the outer wall of the drug storing chamber 201 and hermetically seals the mouth portion 201*a* of the drug storing chamber 201 in such a manner that the capping member is itself rotatable. The inside of the cap body 215 is hollow, is kept liquid-impermeable and non-airtight, and stores a desiccant or a deoxidant. Since the inside of the cap body 215 is kept liquid-impermeable, the solvent does not penetrate into the inside of the cap body 215 when the drug storing chamber 201 and the solvent chamber 202 are brought into communication with each other.

The leg portion 216 is a hollow member having a hexagonal cross section. A recess 217 having a nesting correspondence with the protruding piece 213 is formed at a lower end of the inside of the leg portion 216. Also, a swollen portion 218 is formed at a lower end of the outer surface of the leg portion 216. After the protruding piece 213 engaged with the recess 217 is rotated to break the fragile portion 212 when the leg portion 216 is rotated by the cap body 215 in a direction of an arrow in FIG. 21, the swollen portion 218 abuts with the abutting member 214 to move the protruding piece 213 for driving the protruding piece 213 away from the broken portion, whereby the drug is easily mixed with the solvent.

The drug filling portion 219 for storing the drug is constructed with a cap body 215, an outer surface of the leg portion 216, and an inner surface of the drug storing chamber 201. The moisture or oxygen penetrating into the drug filling portion 219 from outside or from the solvent chamber 202 are adsorbed by the desiccant or deoxidant stored in the inside of the cap body 215 kept non-airtight. After a desiccant or a deoxidant is stored inside the cap body 215, a lid body 220*a* having a suspending device 220 is mounted to its opening edge portion by, for example, thermal welding to provide hermetical sealing.

At the lower end of the solvent chamber 202, there is formed an infusion fluid delivery port 221 to which a later-mentioned drip infusion device 204 can be connected. A rubber plug 223 inserted into the infusion fluid delivery port 221 and having a thin film portion 222 at its center is mounted to the infusion fluid delivery port 221 as shown in FIG. 19. The rubber plug 223 supports the tip portion of the later-mentioned puncture needle 241 and provides a protection so that the thin film portion 222 may not be pierced by the puncture needle 241 during preservation. When the solvent chamber 202 is pushed into the outer barrel 205, the puncture needle 241 penetrates through the thin film portion 222 of the rubber plug 223 to connect the drip infusion device 204 with the solvent chamber 202.

Here, it is possible that the rubber plug 223 does not have a thin film portion 222 at the center. Further, instead of the rubber plug 223, a thin film portion may be resin-molded integrally with the solvent chamber 202 at the infusion fluid delivery port 221.

Figure 23:
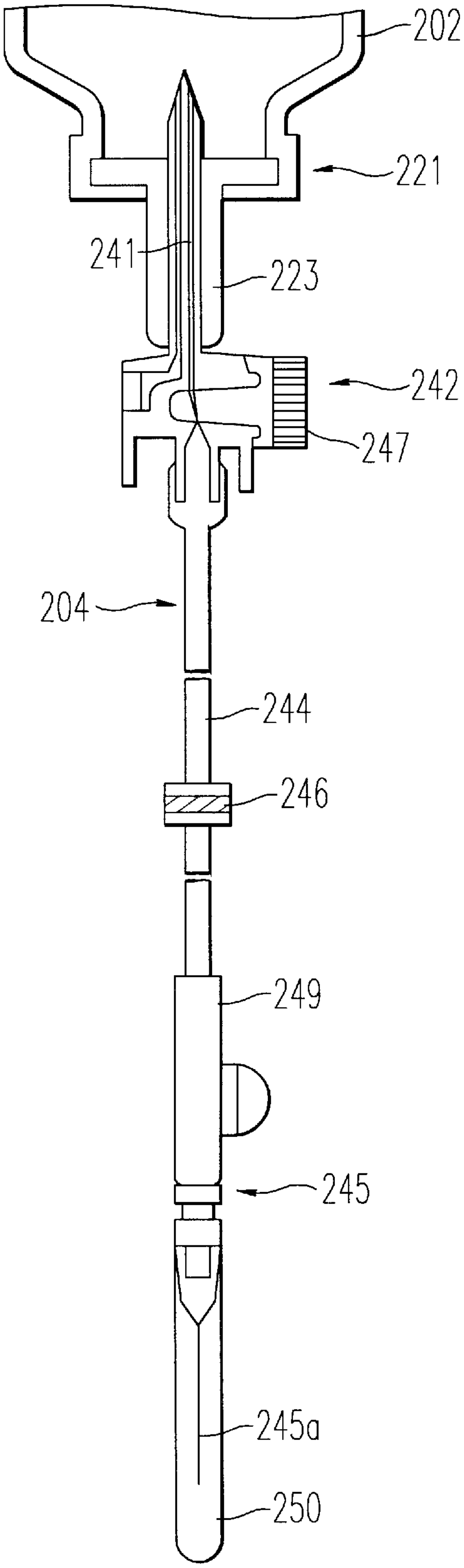
FIG. 23 is a cross-sectional view of an essential part showing a state in which the drip infusion device is connected to the solvent chamber (at the time of infusion).

As shown in FIG. 23, the drip infusion device 204 is constructed with a puncture needle 241, a valve 242 as a flow adjustment device, a tube 244 connected to the valve 242, a needle portion 245, and a filter 246. The puncture needle 241 is capable of piercing the thin film portion 222 of the rubber plug 223 of the infusion fluid delivery port 221 of the bottom portion of the solvent chamber 202.

The puncture needle 241 is a needle made from a synthetic resin and one end of the puncture needle 241 is fixed onto the upper portion of the valve 242. The synthetic resin to be used is preferably a hard resin, such as a high-density polyethylene, an ABS resin, or a polypropylene resin.

Figure 24:
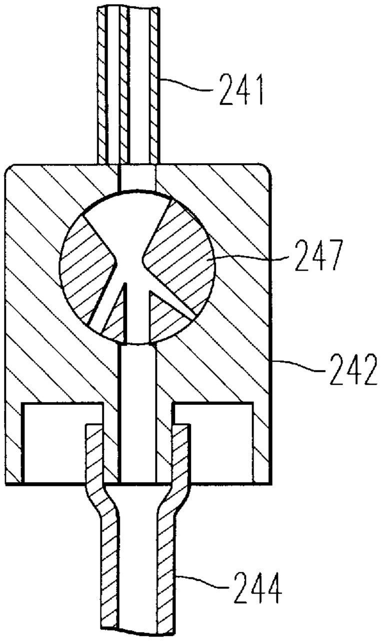
FIG. 24 is a cross-sectional view of an essential part of the flow adjusting device in FIG. 23.

The valve 242 is formed of an opening/closing valve capable of opening and closing the tube passageway and adjusting the flow rate of the infusion fluid in a plurality of levels by switching an internal port through rotation of the knob 247, as shown in FIG. 24. For example, the valve 242 shown in FIG. 24 can adjust the flow rate in three levels. A tube 244 is connected to the lower end of the valve 242.

The tube 244 is a flexible and transparent tube made of synthetic resin and having a total length of about 1 meter. A suitable synthetic resin to be used is a soft resin such as polyvinyl chloride, polypropylene, teflon, polyethylene resin, or the like. To the other end of the tube 244, there is connected an end of the needle portion 245 via a filter 246.

The needle portion 245 has an intravenous injection needle 245*a* fixed onto the lower end thereof for insertion into a human body. Also, the needle portion 245 has a fixing portion 249 disposed on the upper end thereof for fixing the other end of the tube 244. The intravenous injection needle 245*a* is covered by a protecting cap 250.

The filter 246 is provided for removing, from the infusion fluid, minute particles possibly generated for example when the puncture needle 241 of the drip infusion device 204 is connected to the drug storing chamber 201 at the time of conducting the later-mentioned drip infusion. The filter 246 includes a filtering material made of synthetic resin and capable of removing foreign substances having a size of 1 micron or more. The drip infusion device 204 having the puncture needle 241 held at the infusion fluid delivery port 221 is housed in the outer barrel 205 in a sterile manner.

The outer barrel 205 is a bottomed cylindrical container formed integrally with synthetic resin. The outer barrel 205 is formed to have a sufficient thickness which does not allow the container to be deformed easily by external pressing force. The outer barrel 205 is slidably fitted onto a lower portion of the outer surface of the solvent chamber 202 and can be attached to and detached from the lower outer surface of the solvent chamber 202 with the drip infusion device 204 housed therein. A suitable synthetic resin to be used is a hard resin such as polypropylene, polystyrene, high-density polyethylene, polycarbonate resin or the like.

The outer barrel 205 can house the drip infusion device 204 in an airtight manner by engaging with the solvent chamber 202. In the outer barrel 205, there are formed a fixing seat 251 of the valve 242 for holding the tip of the puncture needle 241 near the thin film portion 222 of the rubber plug 223 in the infusion fluid delivery port 221 and a site for fixing other members of the drip infusion device 204 (See FIG. 18). The intravenous injection needle 245*a* covered by the protecting cap 250 is housed between a recess 24 formed in a part of the outer periphery of the solvent chamber 202 and a standing wall portion 252 elevated upwards from a portion of the upper end of the outer barrel 205.

Figure 22:
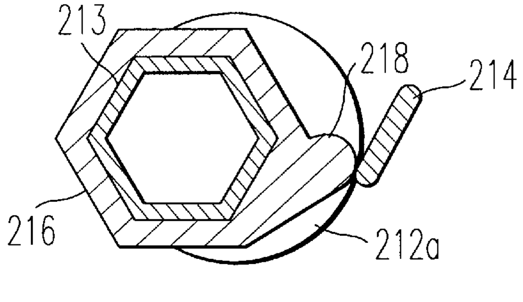
FIG. 22 is a cross-sectional plan view of the protruding piece and the leg portion which are engaged (after the communication is started).

By such a construction, the leg portion 216 is rotated and the protruding piece 213 engaged therewith is twisted to break the fragile portion 212 when the cap body 215 of the capping member 203 is rotated in the direction of an arrow shown in FIG. 4. Further, the swollen portion 218 abuts against the abutting portion 214, whereby a "lever force" having a fulcrum at the abutting point of the swollen portion 218 and the abutting portion 214 acts on the protruding piece 213 to move the protruding piece 213 covering the broken portion, so that the opening 212*a* of the fragile portion 212 is enlarged (FIG. 22). This allows communication between the drug storing chamber 201 and the solvent chamber 202, and by shaking the infusion vessel with the solvent chamber 2 placed at an upper position, the drug is mixed with the solvent for preparation as an infusion fluid.

The fluid apparatus according to this embodiment is constructed in such a manner that the swollen portion 218 and the abutting portion 214 are provided and the protruding piece 213 is moved in a radial direction to enlarge the formed opening 212*a*. However, the above swollen portion 218 and the abutting portion 214 can be omitted and the fluid apparatus may have a simple construction such that the hole portion of the leg portion 216 is rotated to twist the protruding piece 213 for breaking the fragile portion 212.

Figure 25:
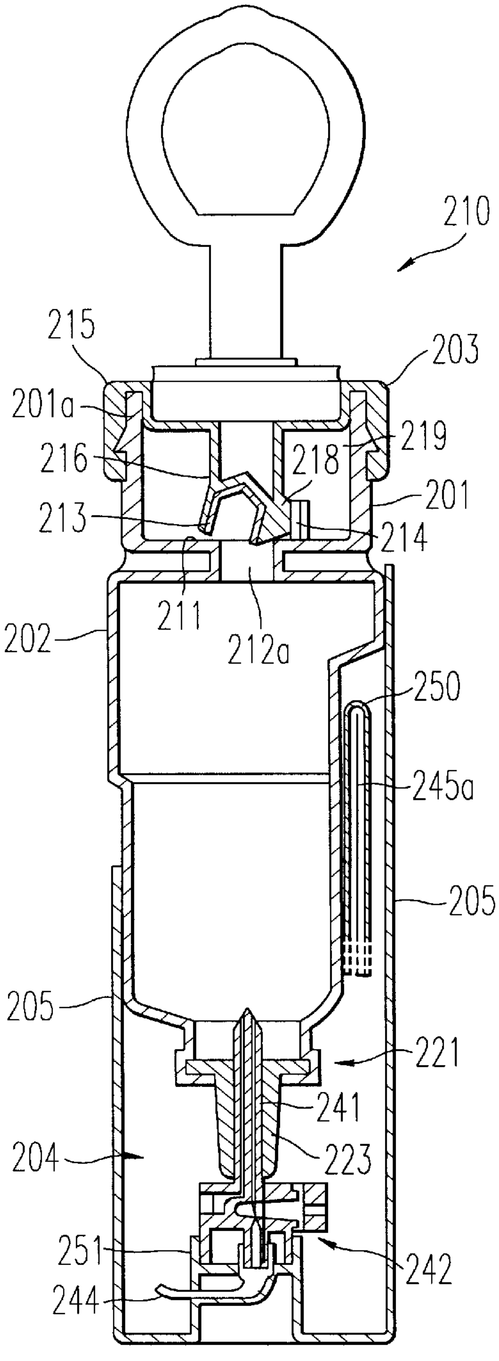
FIG. 25 is a cross-sectional front view of an essential part of the infusion apparatus corresponding to FIG. 19 and showing a state in which the fragile portion of FIG. 19 is broken and the drip infusion device is in communication with the solvent chamber.

Next, the outer barrel 205 slides along the outer peripheral surface of the lower portion of the solvent chamber 202 by pushing the solvent chamber 202 into the outer barrel 205, whereby the puncture needle 241 of the drip infusion device 204 housed in the outer barrel 205 pierces the thin film portion 222 of the rubber plug 223 to allow communication between the drip infusion device 204 and the solvent chamber 202 in a sterile manner, thus enabling the supply of infusion fluid (FIG. 25). This operation can be carried out simply by, for example, allowing the vessel to stand on a desk by itself with the bottom of the outer barrel 205 facing downwards and pushing the solvent chamber 202 from above.

The drip infusion injection is conducted by detaching the outer barrel 205 from the solvent chamber 202, opening the valve 242 housed in the outer barrel, and inserting the intravenous injection needle 245*a* of the drip infusion device 204 into a blood vessel of a patient in conducting the drip infusion. At this time, the drip infusion rate is adjusted by means of the valve 242. Since the liquid amount is adjusted by switching among the passageways in the valve 242, there is no fear that the tube 244 is pressed to be blocked up or to lose the restoring force as in a conventional flow adjustment device in storing the infusion apparatus before use.

Even if minute particles generated in connecting the drip infusion device 204 are mixed into the infusion fluid, it is possible to remove them by means of the filter 246.

Also, since the outer barrel 205 has a bottom and is capable of allowing the infusion apparatus 210 to stand by itself, it is possible to arrange the drip infusion apparatus in order in a standing state for storing the vessels or for allowing them to be on standby.

Thus, in the present invention, the communication between the drug storing chamber 201 and the solvent chamber 202 can be achieved with extreme ease by rotation of the capping member 203. Also, the solvent chamber 202 and the drip infusion device 204 are allowed to be in communication with extreme ease by pushing the solvent chamber 202 into the outer barrel 205.

As described above, since the fragile portion contacting the protruding piece can be broken by rotation of the capping member in the infusion apparatus of the present invention, the communication between the drug storing chamber and the solvent chamber is easily achieved to mix the drug with the solvent.

Further, after the drug is mixed with the solvent, the connection of the drip infusion device is achieved with extreme ease because the puncture needle of the drip infusion device pierces the plug body or the thin film portion of the solvent chamber by displacing the outer barrel relative to the solvent chamber. In case that the tube passageway of the drip infusion device is brought into communication with the solvent chamber by pushing the solvent chamber into the outer barrel, the connection of the drip infusion device is further facilitated.

In case that the drip infusion device is provided with a valve for adjusting the liquid amount by switching among a plurality of passageways, the conventional problem of deformation or poor restoration of the tube due to pressing of the tube is not generated.

Since the fluid apparatus shown above can be integrally molded, the manufacturing process can be simplified, and besides, a complex structure for connecting the drug storing chamber with the solvent chamber can be omitted and the number of components can be reduced, making it possible to provide fluid apparatus at low prices. Also, the transportation costs can be lowered and the storage space can be secured easily.

Also, since neither glass vial nor double-edged needle is used, there is no fear of injuring the hands by mistake. Also, since neither glass nor aluminum is used, it is unnecessary to classify the components in discarding the fluid apparatus, thereby facilitating the discarding process.

Furthermore, since the drip infusion device is housed in the outer barrel engaging with the solvent chamber and the puncture needle of the drip infusion device pierces the plug body or the thin film portion of the solvent chamber by displacing the outer barrel relative to the solvent chamber, the drip infusion device can be connected to the solvent chamber easily and in a sterile manner without injuring the hands.

EXAMPLE 6

Figure 26:
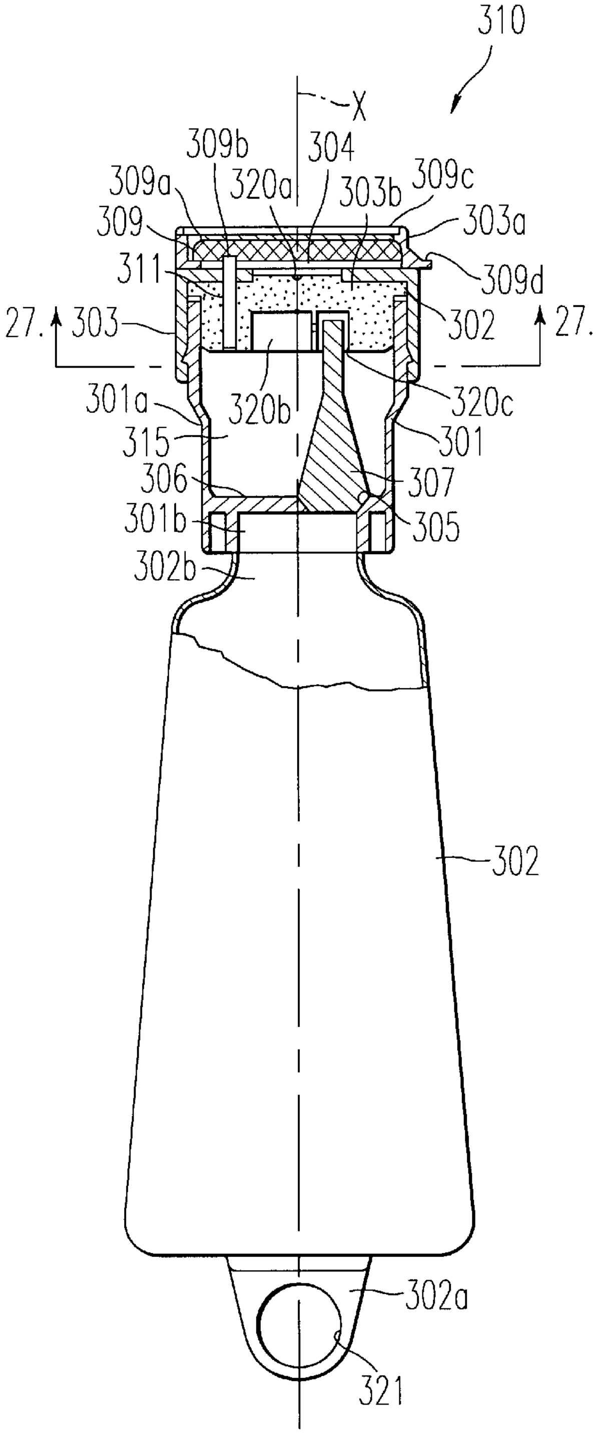
FIG. 26 is a front view including a cross-sectional view of an essential part of the infusion vessel according to Example 6 of the present invention.
Figure 27:
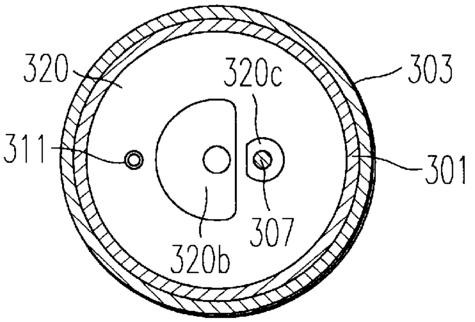
FIG. 27 is a cross-sectional view of FIG. 26 along the line 27—27.

A infusion vessel 310 shown in FIG. 26 is mainly constructed with a drug storing chamber 301, a solvent chamber 302, and a capping member 303 mounted to the drug storing chamber 301 and having a drug solution delivery portion 304.

The drug storing chamber 301 is a wide-mouth vessel including, at the upper end thereof, a mouth portion 301*a* to which the capping member 303 can be mounted, and at the bottom portion 306, a communication hole 305 mentioned later. The drug storing chamber 301 is integrally molded with polypropylene.

The solvent chamber 302 is formed into a liquid-impermeable bag-like shape with transparent sheets of polypropylene or a copolymer of polypropylene and polyethylene to have a sufficient flexibility. At an upper portion of the solvent chamber 302, there is formed a mouth portion 302*b* which is connected to a port 301*b* formed at the lower portion of the drug storing chamber 301. At a peripheral portion 302*a* of a lower end of the solvent chamber 302, there is formed a suspending hole portion 321 as a suspension support portion. The drug storing chamber 301 and the solvent chamber 302 are connected by, for example, heat-welding the port 301*b* of the drug storing chamber 301 and the mouth portion 302*b* of the solvent chamber 302. Alternatively, the drug storing chamber 301 and the solvent chamber 302 may be integrally molded.

At the drug storing chamber's bottom portion 306 connecting the drug storing chamber 301 with the solvent chamber 302 in a liquid-impermeable manner, there is formed a communication hole 305 for connecting the drug storing chamber 301 with the solvent chamber 302. A solid and approximately conical protruding piece 307 which seals the communication hole 305 and which protrudes into the drug storing chamber 301 is connected to the communication hole 305 with the center X of the vessel being shifted (eccentrically). The protruding piece 307 is formed with a mixture of polyethylene and polypropylene which is a molding material having a poor compatibility with propylene which is a molding material of the drug storing chamber 301. so that the protruding piece 307 is a little more fragile than the drug storing chamber 301. However, the protruding piece 307 is integrally formed with the bottom portion 306 substantially as a part of the drug storing chamber 301. For example, the drug storing chamber 301 and the protruding piece 307 can be molded as one component having the bottom portion 306 of the drug chamber 301 integrally connected with the protruding piece 307 by mounting the previously formed protruding piece 307 onto a mold and then casting a resin for forming the drug storing chamber 301 portion. The size of the communication hole 305 is preferably 5 to 15 mm in diameter.

The lower portion of the inside wall of the capping member 303 is coupled to the outer wall of the drug storing chamber 301 and hermetically seals the mouth portion 301*a* of the drug storing chamber 301 so that the capping member 303 is itself rotatable. In the lid portion 303*a* of the capping member 303, there is formed a cut hole 303*b* serving as a drug solution delivery portion capable of being pierced by a puncture needle connected to one end of the drip infusion device. Also, the upper portion of the lid portion 303*a* includes a flat surface which allows the infusion vessel 310 filled with a drug and a solvent to stand by itself.

A rubber plug (plug body) 320 of the capping member 303 is inserted into the mouth portion 301*a* of the drug storing chamber 301 for keeping the drug storing chamber 301 airtight. Approximately at the center of the rubber plug 320, there is formed a recess 320*a* being in correspondence with the cut hole 303*b* and facilitating the penetration of the puncture needle. Though the recess 320*a* is exposed at the cut hole 303*b*, the cut hole 303*b* is protected by a later-mentioned chamber 309 for storing a drug alteration preventive agent so that the surface of the rubber plug 320 may not be contaminated. The recess 320*a* appears via the cut hole 303*b* when the storing chamber 309 is removed.

In the lower surface of the rubber plug 320, there are formed a lower recess 320*b* for facilitating the piercing of the puncture needle and an engaging hole 320c for engaging with (the upper end of) the protruding piece 307. The engaging hole has a diameter of 2 to 5 mm.

Meanwhile, a chamber 309 for storing a drug alteration preventive agent is connected to the lid portion 303*a* of the capping member 303 in such a manner as to cover the lid portion 303*a*. The storing chamber 309 stores a desiccant (for example, a silica gel) 309*a* and a deoxidant (for example, an active iron oxide) 309*b*. Here, the reference numeral 309*c* represents an upper lid of the storing chamber 309, and the reference numeral 309*d* represents a puller-piece to be used in removing the storing chamber 309 from the capping member 303.

A narrow tube 311 is provided through the lid portion 303*a* and the rubber plug 320 of the capping member 303. The narrow tube 311 is formed of polyethylene or polypropylene, and a hydrophobic filter (for example, a sintered body of polypropylene) is inserted into a lower portion of the narrow tube 311. The inner diameter of the narrow tube is 1 to 3 mm.

The drug filling portion 315 for storing the drug is substantially a space partitioned by the rubber plug 320 and the drug storing chamber 301. The moisture and oxygen penetrating into the drug filling portion 315 from outside or from the solvent chamber is adsorbed by a desiccant 309*a* and a deoxidant 309*b* stored in the chamber 309 for storing a drug alteration preventive agent via the narrow tube 311 which is kept non-airtight by the hydrophobic filter 311*a*, thereby to prevent the alteration of the drug.

The drug storing chamber 301 is fabricated by loading the drug filling portion 315 with a drug, inserting the rubber plug 320 of the capping member 303 into the mouth portion 301*a* to allow the engaging hole 320*c* to be engaged with the protruding piece 307, coupling the lid portion (outer frame) 303*a* of the capping member, then mounting the narrow tube 311 through the lid portion 303*a* and the rubber plug 320 of the capping member (Here, a small hole is formed beforehand in the lid portion 303*a* and the rubber plug 320 of the capping member to allow insertion of the narrow tube 311), and attaching the chamber 309 for storing a drug alteration preventive agent from above the capping member 303 by heat-fusion or the like so as to cover the upper end opening of the narrow tube 311 and the cut hole 303*b* of the capping member 303 so that the storing chamber can be easily detached.

Here, although the chamber 309 for storing a drug alteration preventive agent is provided in this Example, the storing chamber 309 need not be necessarily provided depending on the kind of the drug to be stored in the drug storing chamber 301, and it suffices to provide an upper lid 309*c* having a puller-piece 309*d* in the capping member 303.

Figure 28:
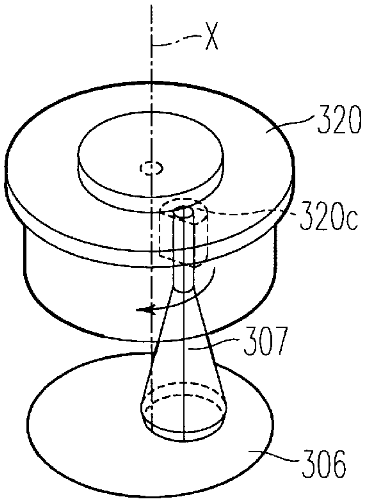
FIG. 28 is a schematic view for explaining the state in which the protruding piece of FIG. 26 is let to fall for forming the communication hole.

By such a construction, when the capping member 303 is rotated in using the vessel, the rubber plug 320 rotates in accordance therewith, and the protruding piece 307 rotating via the engaging hole 320*c* of the rubber plug 320 is twisted to be torn off from the bottom portion 306 of the drug storing chamber 301, whereby a large communication hole 305 is easily formed between the drug storing chamber 301 and the solvent chamber 302 (See especially FIG. 28).

Then, the solvent flows into the drug storing chamber 301 via the communication hole 305 by allowing the vessel to stand with the chamber 309 for storing a drug alteration preventive agent facing downwards or by pressing the solvent chamber 302, whereby the drug is mixed with the solvent. Subsequently, the drug solution obtained by mixing the drug with the solvent is taken out as an infusion fluid at one end of the drip infusion device by removing the chamber 309 for storing a drug alteration preventive agent with the puller-piece 309*d* to open the cut hole 303*b* serving as the drug solution delivery portion 304, inserting into the exposed recess 320*a* of the rubber plug 320 the puncture needle connected to the other end of the drip infusion device to pierce the rubber plug 320, and hanging the suspending hole portion 321 of the solvent chamber 302 onto a stand. Here, the vessels 310 can be stored in arrangement or allowed to be on standby if the vessels 310 are let to stand by themselves so that the flat surface of the chamber 309 for storing a drug alteration preventive agent or the lid portion 303*a* after the removal of this storing chamber may face downwards.

As shown in the above Example, the communication between the drug storing chamber 301 and the solvent chamber 302 is achieved with extreme ease by the rotation of the capping member 303.

Thus, in the infusion vessel 310, when the capping member 303 is rotated about the mouth portion 301*a* of the drug storing chamber 301, the rubber plug 320 rotates in accordance therewith to twist and tear off the protruding piece 307 engaging with the engaging portion of the rubber plug 320 from the bottom portion 306 of the drug storing chamber 301 to open the communication hole 305, whereby the drug storing chamber 301 and the solvent chamber 302 are easily brought into communication to mix the drug with the solvent.

As shown above, according to the infusion vessel, the drug storing chamber and the solvent chamber are brought into communication to provide the infusion fluid easily and in a sterile manner, since the protruding piece hermetically seals the communication hole disposed at the bottom portion of the drug storing chamber and the protruding piece engaging with the plug body is twisted to be torn off from the bottom portion via the plug body by the rotation of the capping member to open the communication hole.

The communication hole can be opened at a time and with certainty simply by rotating the capping member in using the vessel in case that an engaging hole is formed as an engaging portion of the plug body and further the engaging hole and the protruding piece engaging with the engaging hole are formed eccentrically from the center of the drug storing chamber.

According to this infusion vessel, since the drug solution delivery portion is formed in the capping member, the conventional step of separately preparing and mounting the drug solution delivery portion to the lower portion of the solvent chamber will be unnecessary. Also, it will be unnecessary to dispose the suspension support portion to the capping member by molding integrally or by bonding. The vessel can be suspended and used for infusion simply by opening a suspending hole portion as a suspension support portion in the lower part of the solvent chamber.

According to this fluid apparatus, the manufacturing process can be simplified, and besides, a complex structure for connecting the drug storing chamber with the solvent chamber can be omitted and the number of components can be reduced, making it possible to provide fluid apparatus at low prices. Also, the transportation costs can be lowered and the storage space can be secured easily.

Also, since no glass vial or double-edged needle is used, there is no fear of injuring the hands by mistake at the time of classifying the components in discarding the fluid apparatus. Also, since no glass or aluminum is used, it is unnecessary to classify the components in discarding the fluid apparatus, thereby facilitating the discarding process.

EXAMPLE 7

Figure 29:
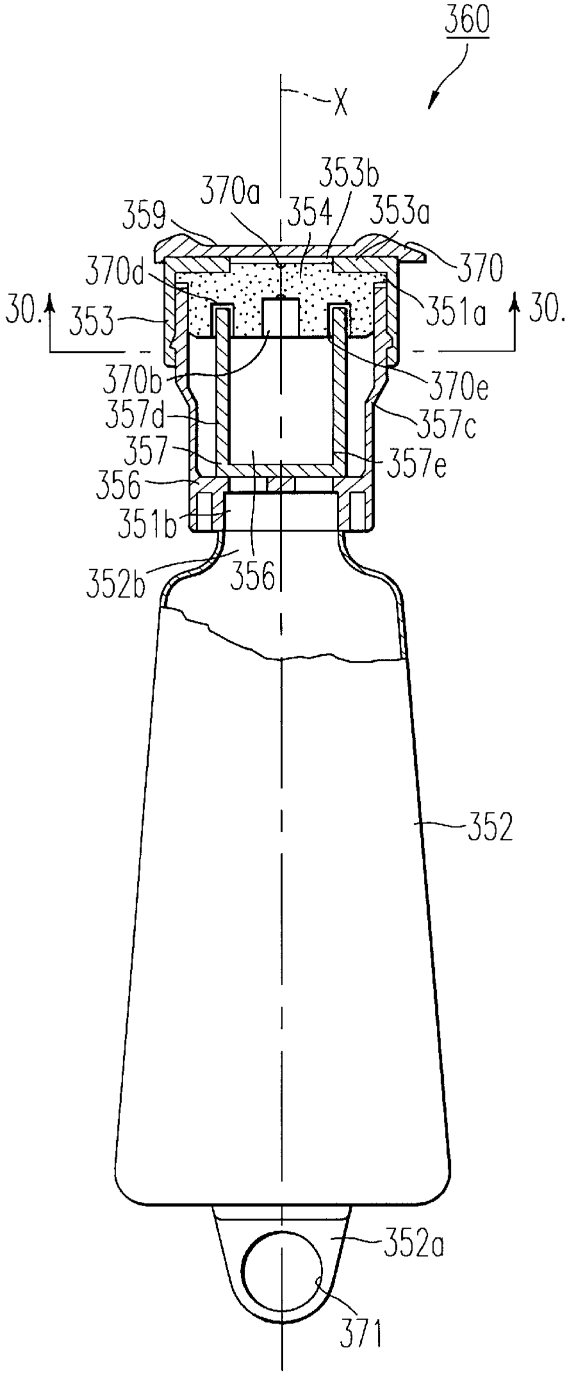
FIG. 29 is a front view including a longitudinal cross-sectional view of an essential part of the infusion vessel according to Example 7 of the present invention.
Figure 30:
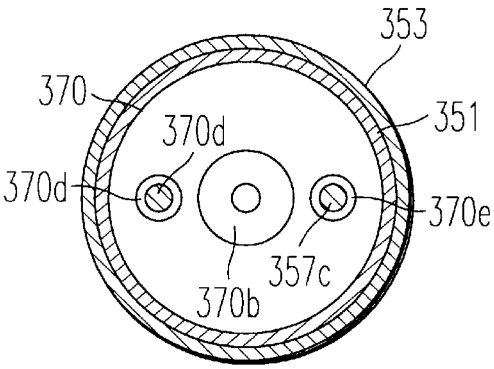
FIG. 30 is a cross-sectional view of FIG. 29 along the line 30—30.
Figure 32:
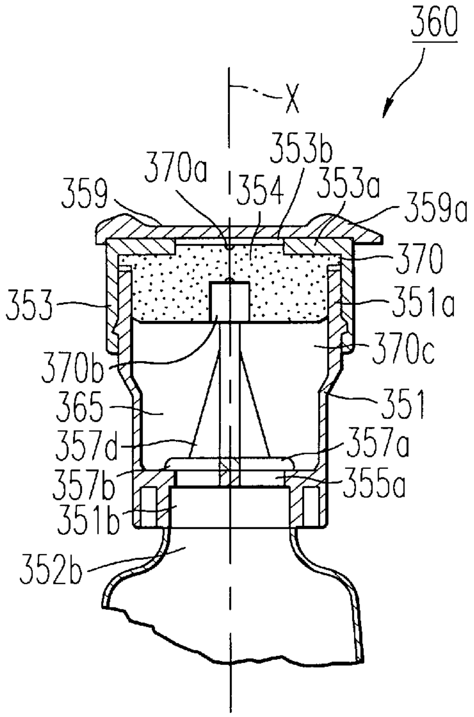
FIG. 32 is a longitudinal cross-sectional view of an essential part showing a different state.
Figure 31:
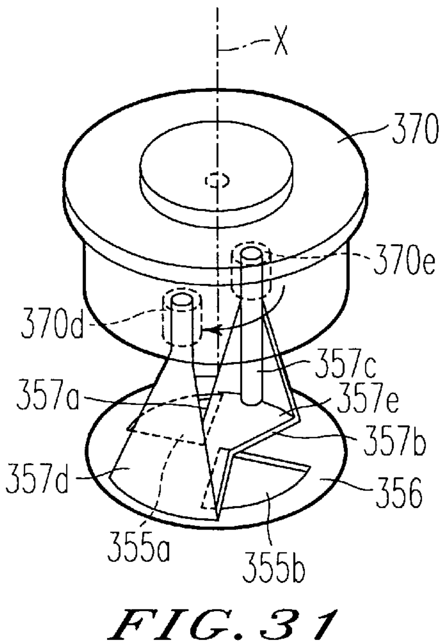
FIG. 31 is a view corresponding to FIG. 28 and showing a different state.
Figure 33:
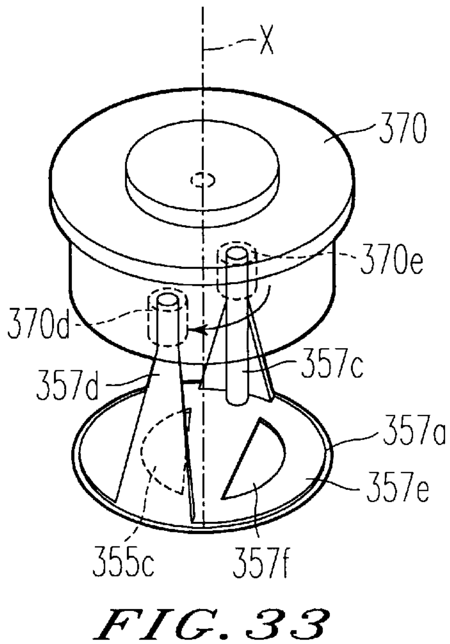
FIG. 33 is a view corresponding to FIG. 31 according to Example 8 of the present invention.
Figure 34:
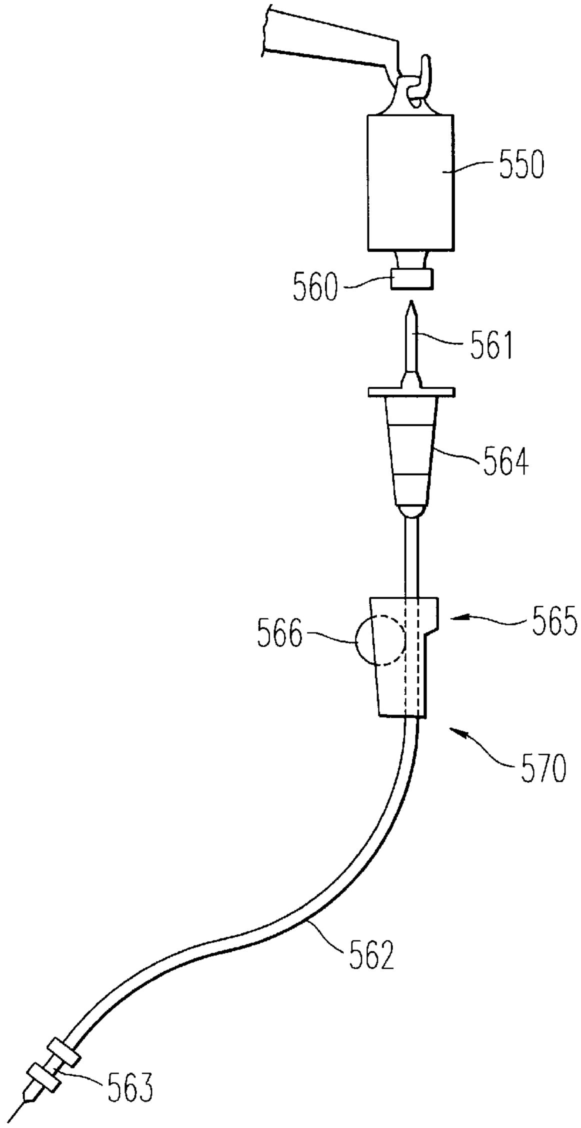
FIG. 34 is an explanatory view for showing an example of conventional drip infusion device connected to the infusion apparatus.
Figure 35:
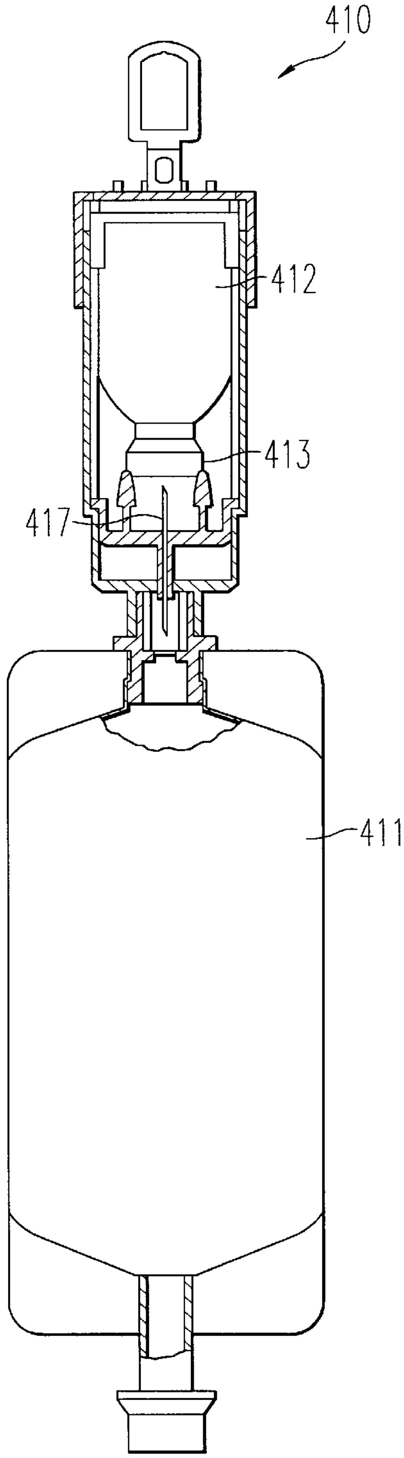
FIG. 35 is a cross-sectional view of an essential part showing an example of conventional infusion vessel.
Figure 36:
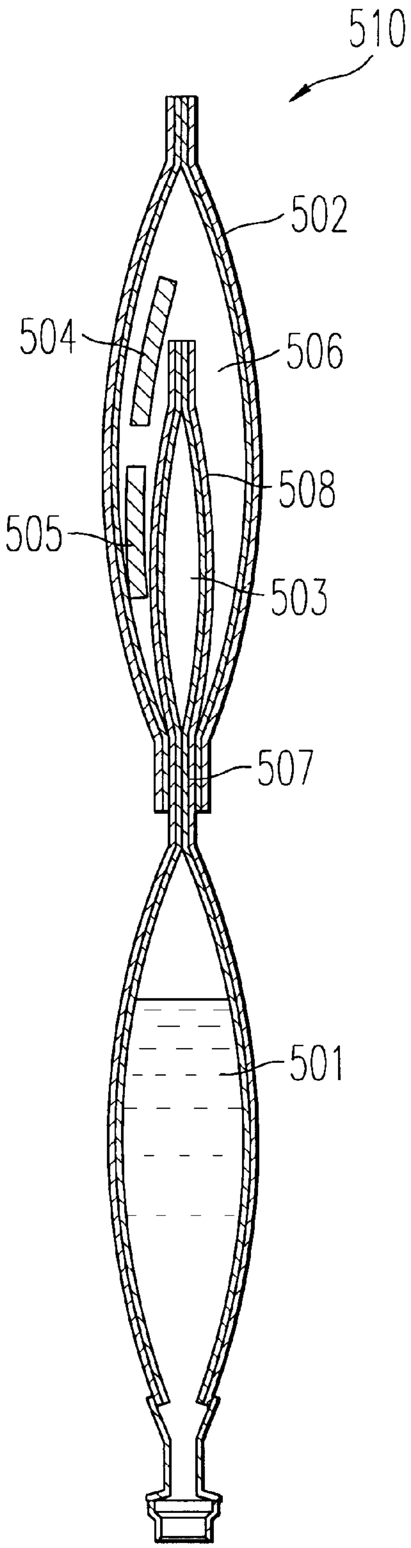
FIG. 36 is a cross-sectional view of an essential part showing another example of conventional infusion vessel.

An alternative example which is different from the above Example 6 is as follows. FIGS. 29–32 illustrate this example wherein the reference numbers used for example 6 are labeled, but wherein the reference numbers increased by fifty. Referring to FIGS. 29–32, a protruding piece 357 having fan-like cut portions (or openings) 357*a*, 357*b* at the bottom 357*e* is brought into close contact with a bottom portion 356 of the drug storing chamber 351. Also illustrated in the Example is recess 370*a*, delivery portion 354, capping member 353*b*, lid portion 353*a*, dessicant 359*a*, mouth portion 351*a*, pherial portion 352*a*, suspending hole portion 371, mouth portion 352*b* for the solvent chamber, portion 351*b*, drug filling portion 365, lower recess 370*b*, chamber 59 and engaging hole 370*c*. By the rotational movement of the protruding piece 357, the cut portions 357*a*, 357*b* of the protruding piece 357 are allowed to overlap a pair of fan-like communication holes 355*a*, 355*b* formed at the bottom portion 356 of the drug storing chamber 351, whereby the drug storing chamber 351 and the solvent chamber 352 are brought into communication. Here, the reference numerals 357*c*, 357*d* represent tower portions of the protruding piece 357, and tip portions thereof are inserted into engaging holes 370*d*, 370*e* formed in the rubber plug 370 of the capping member 353. Accordingly, although the communication holes 355*a*, 355*b* are closed and blocked in a liquid-impermeable manner by the bottom portion 357*e* of the protruding piece 357 before use as shown in FIG. 29, the protruding piece 357 rotates via the engaging holes 370*d*, 370*e* and the tower portions 357*c*, 357*d* in accordance with the rotational movement of the capping member 353 as shown in FIG. 31, whereby the communication holes 355*a*, 355*b* are allowed to overlap the cut portions 357*a*, 357*b* for achieving communication as shown in FIG. 32.

Here, the protruding piece 357 is molded with a mixture of polypropylene resin in 10 to 30% and polyethylene resin in 90 to 70%, and the drug storing chamber 351 is molded with polypropylene resin in 100%. These are bonded with resin (provisionally fixed) so as to secure the tightness of the communication holes 355*a*, 355*b* until the drug is mixed with the solvent. The fan-like communication holes 355*a*, 355*b* formed at the bottom portion 356 of the drug storing chamber 351 are formed to oppose each other relative to the center of the bottom portion 356 and each have a central angle of about 90°. The fan-like cut portions 357*a*, 357*b* formed at the bottom part 357*e* of the protruding piece 357 are formed to have the same shape and configuration as the above communication holes 355*a*, 355*b*.

As shown above, since the infusion vessel of FIGS. 29–32 have cut portions 357*a*, 357*b* formed beforehand in correspondence with the communication holes 355*a*, 355*b*, it is possible to establish a large opening, whereby the drug can be mixed with the solvent with certainty in a short time. Moreover, the infusion fluid can be safely supplied because few minute fragments of resin are generated due to detachment by twisting.

Further, instead of the cut portions 357*a*, 357*b* of the protruding piece 357, a semicircular opening 357*f* may be formed as shown in FIG, 33, and in correspondence therewith, a pair of communication holes formed at the bottom portion 356*a* of the drug storing chamber may be a semicircular communication hole 355*c*.

As shown above, according to this infusion vessel, the drug storing chamber and the solvent chamber are brought into communication in a short time and with certainty and the infusion fluid can be supplied easily, safely, and in a sterile manner, since the protruding piece hermetically seals the communication holes provided at the bottom of the drug storing chamber, and by the rotation of the lid portion of the capping member, the protruding piece engaging with the plug body is slidingly rotated, whereby the communication holes are opened via the cut portions or the openings formed in the protruding piece.

What we claim is:

1. A fluid vessel comprising:

a drug storing chamber, a capping member for hermetically sealing a mouth portion of the drug storing chamber, and a solvent chamber connected to a bottom portion of the drug storing chamber such that at least a portion of said drug storing chamber is positioned outside said solvent chamber, wherein the drug storing chamber is provided with a communication hole at the bottom portion thereof for communicating with the solvent chamber and includes a protruding piece which hermetically seals the communication hole, protrudes into the drug storing chamber and is movable so as to open the communication hole, and wherein the capping member has an engaging portion engageable with a tip of the protruding piece such that the protruding piece is movable to open the communication hole by rotation of the capping member.

2. A fluid vessel according to claim 1, wherein the capping member comprises a pierceable plug body and a lid body optionally attached to the plug body, the plug body including an engaging portion engagable with the tip portion of the protruding piece.

3. A fluid vessel according to claim 2, wherein the protruding piece is disposed eccentrically from the center of the drug storing chamber and the engaging portion comprises an engaging hole which is formed in accordance at a bottom surface portion of the plug body and which receives tip portion of the protruding piece.

4. A fluid vessel according to claim 2, wherein the capping member comprises a chamber detachably located at a lid portion thereof and comprises a narrow tube formed through the plug body for allowing communication between the chamber for storing a drug alteration preventive agent and the drug storing chamber via a hydrophobic filter.

5. A fluid vessel according claim 4, wherein the chamber comprise a chamber within which is storable a drug alteration preventive agent having a desiccant and/or a dexiodant.

6. A fluid vessel according to claim 1, wherein the communication hole comprises first and second holes formed with axial symmetry and wherein the protruding piece includes a bottom portion which hermetically seals the two holes in such a manner that the bottom portion can be moved to open the first and second holes.

7. A fluid vessel according to claim 6, wherein the bottom portion of the protruding piece includes one of an opening and a cut portion which is formed corresponding with the shape of the communication hole and which is openable to the communication hole by a sliding movement accompanying the rotation of the capping member.

8. A fluid vessel according to claim 1, wherein the communication hole comprises a semicircular hole and the protruding piece includes a bottom portion which hermetically seals the hole in such a manner that the bottom portion is movable to open the hole.

9. A fluid vessel according to claim 1, wherein the protruding piece integrally protrudes into the drug storing chamber via a fragile portion which is breakable by rotation of the capping member in a peripheral portion of the communication hole at the bottom portion of the drug storing chamber.

10. A fluid vessel according to claim 6, wherein the capping member includes a leg portion extending into the drug storing chamber.

11. A fluid vessel according to claim 10, wherein the protruding piece is engageable with the leg portion of the capping member upon insertion of the tip of the protruding piece into the leg portion.

12. A fluid vessel according to claim 11, wherein a lower portion of the leg portion includes a swollen portion formed in part of a peripheral surface thereof and the drug storing chamber comprises an abutting portion which is formed at a bottom portion thereof and which is abuttable with the swollen portion to move the protruding piece so as to open the communication hole after the fragile portion is broken by rotation of the capping member.

13. A fluid vessel according to claim 12, wherein the leg portion is formed eccentrically with respect to the center of the lid portion.

14. A fluid vessel according to claim 10, wherein the leg portion includes inner threaded portion and the protruding piece includes a screw threaded portion which is screw engageable with the inner thread portion, such that the protruding piece is movable upwards to open the communication hole by rotation of the capping member.

15. A fluid vessel according to claim 1, wherein the protruding piece is formed of a material having poor compatiability with a material for forming the drug storing chamber and is connected to the communication hole so that the protruding piece can be twisted so as to be torn off by rotation of the capping member.

16. A fluid vessel according to claim 15, wherein the drug storing chamber contains polypropylene, and the protruding piece contains a mixture of polyethylene and polypropylene, a copolymer of polyethylene, or a graft polymer as a major component, and wherein the drug storing chamber and the protruding piece are welded together.

17. A fluid vessel according to claim 1, wherein the drug storing chamber stores a drug and the solvent chamber stores a solvent.

18. A fluid vessel according to claim 1, wherein the capping member comprises a self-supporting member holding the vessel in a self-standing state.

19. A fluid vessel according to claim 1, wherein the solvent chamber includes a suspension support portion formed at a lower end thereof for suspending the vessel with the capping member side facing downwards.

20. A fluid apparatus comprising:

a fluid vessel according to claim 1 in which the solvent chamber is provided with an infusion fluid delivery portion formed at a lower end thereof and has one of a pierceable thin film portion and a pierceable plug body;

a drip infusion device having a needle portion at one end thereof and having, at the other end thereof, a puncture needle for piercing the plug body or the thin film portion of the solvent chamber; and a bottomed outer barrel housing the drip infusion device and being displaceably attachable to and detachable from the solvent chamber, the outer barrel enabling the puncture needle of the drip infusion device to pierce said one of the plug body and the thin film portion of the solvent chamber by displacing the outer barrel relative to the solvent chamber after the drug storing chamber and the solvent chamber are brought into communication by rotation of the capping member to mix the drug with the solvent.

21. A fluid apparatus according to claim 20, wherein the outer barrel is slidably engageable with the solvent chamber and the puncture needle of the drip infusion device pierces said one of thin film portion and the plug body of the solvent chamber by pushing the solvent chamber into the outer barrel after the drug is mixed with the solvent.

22. A fluid apparatus according to claim 21, wherein the drip infusion device comprises a valve for adjusting the amount of fluid flowing through the tube by switching among a plurality of passageways.

* * * * *